United States Patent
Snyder et al.

(10) Patent No.: US 8,080,367 B2
(45) Date of Patent: Dec. 20, 2011

(54) REGULATION OF CELL SURVIVAL BY HSP90 AND IP6K2

(75) Inventors: Solomon H. Snyder, Baltimore, MD (US); Anutosh Chakraborty, Baltimore, MD (US); Michael Koldobskiy, Baltimore, MD (US); Katherine Sixt, Baltimore, MD (US); Krishna Juluri, Baltimore, MD (US); Asif K Mustafa, Baltimore, MD (US); Damian B Van Rossum, University Park, PA (US); Randen L Patterson, University Park, PA (US)

(73) Assignee: The Johns Hopkins University, Baltimore, MD (US)

( * ) Notice: Subject to any disclaimer, the term of this patent is extended or adjusted under 35 U.S.C. 154(b) by 202 days.

(21) Appl. No.: 12/514,254

(22) PCT Filed: Dec. 11, 2007

(86) PCT No.: PCT/US2007/025246
§ 371 (c)(1),
(2), (4) Date: Sep. 3, 2009

(87) PCT Pub. No.: WO2008/073382
PCT Pub. Date: Jun. 19, 2008

(65) Prior Publication Data
US 2010/0129806 A1    May 27, 2010

Related U.S. Application Data

(60) Provisional application No. 60/869,496, filed on Dec. 11, 2006.

(51) Int. Cl.
*C12Q 1/00* (2006.01)
(52) U.S. Cl. .................................................. 435/4
(58) Field of Classification Search ................. None
See application file for complete search history.

(56) References Cited

OTHER PUBLICATIONS

Morrison et al (JBC, 2001, 276(27): 24965-24970.*
Chakraborty et al (PNAS, Jan. 2008, 105(4):1134-1139).
Shames et al (PNAS, Feb. 2008, 105(5): 1389-1390).
International Search Report Issued Jul. 29, 2008 for PCT/US2007/025246 (WO 2008/073382 A3).

* cited by examiner

*Primary Examiner* — Sean Aeder
(74) *Attorney, Agent, or Firm* — Banner & Witcoff, Ltd.

(57) ABSTRACT

Anti-cancer drugs are identified by screening for agents and compounds which inhibit the binding of HSP90 and IP6K2. In vitro and in vivo assays can be used. Any phenomenon associated with the binding or inhibition can be monitored, including cell death, subcellular localization, catalytic activity of IP6K2, and IP7 formation.

2 Claims, 15 Drawing Sheets

K2  131 WVRQHRKEE-K 140
P23 104 WPRLTK-ERAK 113
FIG. 1A
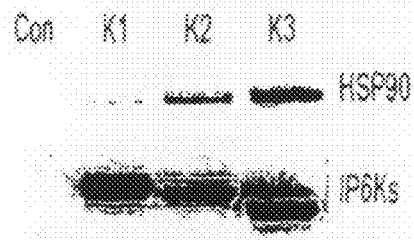
FIG. 1B
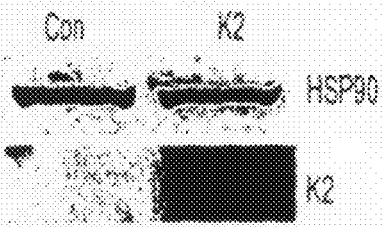
FIG. 1C
FIG. 1D
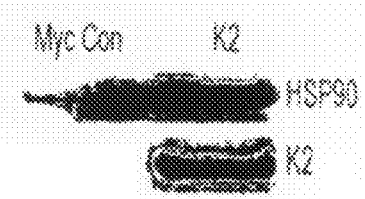
FIG. 1E
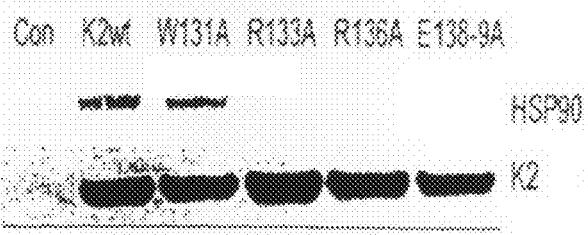
FIG. 1F

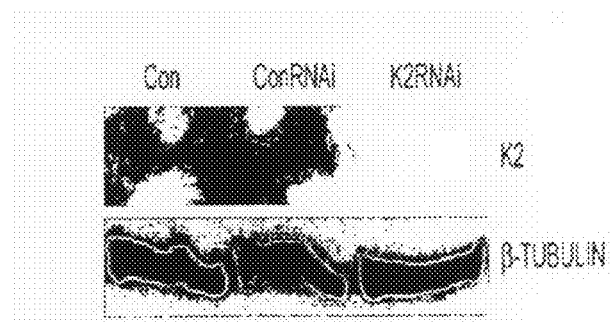
FIG. 10A
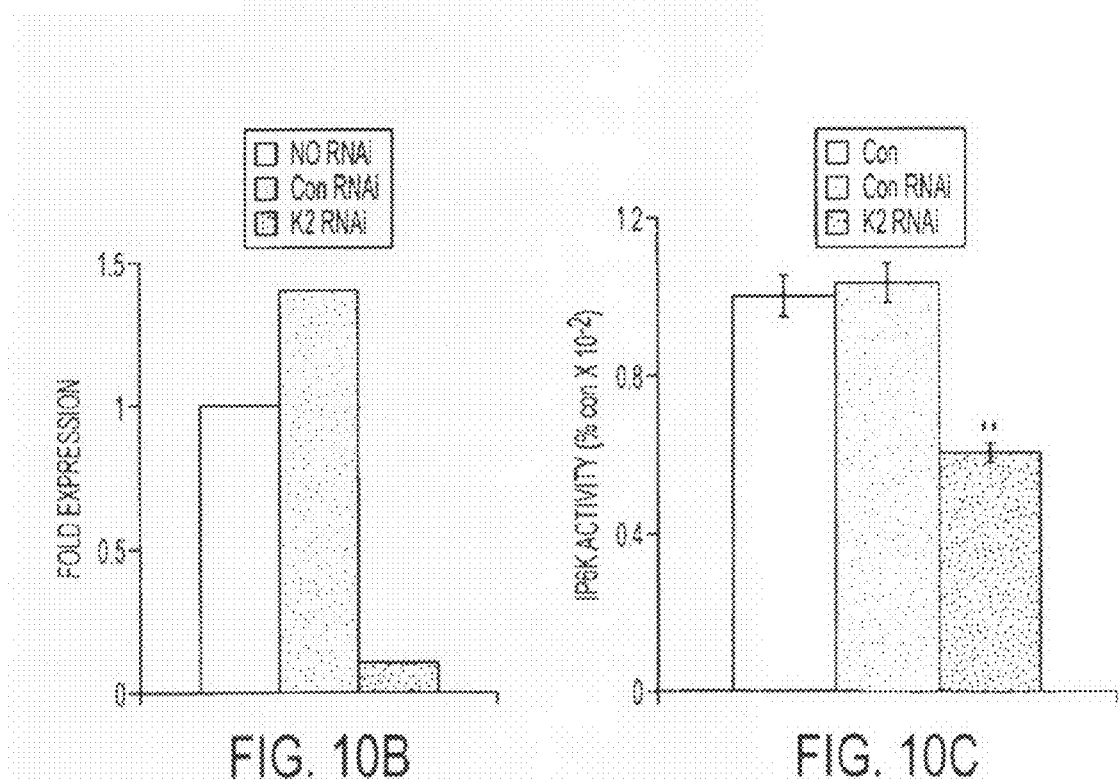
FIG. 10B
FIG. 10C

REGULATION OF CELL SURVIVAL BY HSP90 AND IP6K2

This work was supported with funds from the U.S. government via U.S. Public Health Service Grant MH18501, Conte Center Grant MH068830-02, and Research Scientist Award DA00074. The U.S. government therefore retains certain rights in the invention.

TECHNICAL FIELD OF THE INVENTION

This invention is related to the area of protein-protein interactions. In particular, it relates to cancer drug screening

BACKGROUND OF THE INVENTION

Inositol phosphates are major intracellular signaling molecules with the best known of these, inositol 1,4,5-trisphosphate, releasing intracellular calcium (1, 2). Among inositol phosphates recent attention has focused upon higher inositol polyphosphates (3-6) including the pyrophosphate diphosphoinositol pentakisphosphate (5-PP-IP5, IP7), which is able to donate its energetic phosphate to various protein targets (7). In vivo, IP7 is generated by a family of three inositol hexakisphosphate kinases (IP6K) (8-9) of which IP6K2 has been associated with apoptosis. Thus, apoptotic stimuli markedly increase IP7 formation, overexpression of IP6K2 augments cell death, and siRNA-induced depletion promotes cell survival (10-12). In addition to their classic role in promoting refolding of denatured proteins, heat shock proteins (HSP) are implicated in anti-apoptotic cascades (13-17) and have been targets for the development of anti-cancer drugs (18-22). There is a continuing need in the art to identify new drugs for treating cancer.

SUMMARY OF THE INVENTION

According to one embodiment of the invention a method is provided for identifying compounds which interfere with the binding of IP6K2 protein to HSP90 protein. Such compounds are candidate therapeutic agents. A first protein, a second protein, and a test compound are contacted with each other under conditions in which the first and second proteins would bind to each other if in the absence of test compound. The first protein comprises IP6K2 protein and the second protein comprises HSP90 protein or the first protein comprises HSP90 protein and the second protein comprises IP6K2 protein. The quantity of the first protein which is bound to, is displaced from, or is prevented from binding to, the second protein is determined. A candidate therapeutic agent is identified if a compound diminishes the quantity of the first protein bound to the second protein, or displaces first protein bound to the second protein, or prevents first protein from binding to the second protein.

According to another embodiment of the invention a method is provided for identifying compounds which interfere with the binding of IP6K2 protein to HSP90 protein. Such compounds are candidate therapeutic agents. A first polypeptide, a second polypeptide, and a test compound are contacted with each other. At least one of said first and said second polypeptides is a polypeptide which comprises less than all of the complete sequence of amino acids of HSP90 protein or IP6K2 protein. Each of said polypeptides contains a sufficient portion of HSP90 protein or IP6K2 protein to bind to the other polypeptide. When said first polypeptide is HSP90 protein or a polypeptide which comprises less than all of the complete sequence of amino acids of HSP90 protein, then said second polypeptide is IP6K2 protein or a polypeptide which comprises less than all of the complete sequence of amino acids of IP6K2 protein. When said first polypeptide is IP6K2 protein or a polypeptide which comprises less than all of the complete sequence of amino acids of IP6K2 protein, then said second polypeptide is HSP90 protein or a polypeptide which comprises less than all of the complete sequence of amino acids of HSP90 protein. The quantity of the first polypeptide which is bound to, is displaced from, or is prevented from binding to, the second polypeptide is determined. A test compound which diminishes the quantity of the firstprotein, or which prevents first protein from binding to the second protein, or which displaces first protein from binding to the second protein, is identified as a candidate therapeutic agent.

Another aspect of the invention is a method of identifying compounds which interfere with the binding of human IP6K2 protein to human HSP90 protein. A cell is contacted with a test compound. The cell comprises three recombinant DNA constructs. The first construct encodes a first polypeptide fused to a sequence-specific DNA-binding domain. The second construct encodes a second polypeptide fused to a transcriptional activation domain. The third construct comprises a reporter gene downstream from a DNA element which is recognized by the sequence-specific DNA-binding domain. The first polypeptide is an IP6K2 polypeptide and said second polypeptide is an HSP90 polypeptide, or said first polypeptide is a HSP90 polypeptide and said second polypeptide is a IP6K2 polypeptide; wherein said polypeptides contain a sufficient portion of HSP90 protein and IP6K2 protein to bind to the other polypeptide. The quantity of expression of the reporter gene is determined in the presence of said compound.

Yet another aspect of the invention is a cell which comprises three recombinant DNA constructs: the first construct encodes a first polypeptide fused to a sequence-specific DNA-binding domain; the second construct encodes a second polypeptide fused to a transcriptional activation domain, the third construct comprises a reporter gene downstream from a DNA element which is recognized by said sequence-specific DNA-binding domain. The first polypeptide is an IP6K2 polypeptide and the second polypeptide is a HSP90 polypeptide, or said first polypeptide is a HSP90 polypeptide and said second polypeptide is an IP6K2 polypeptide. The polypeptides contain a sufficient portion of HSP90 protein and IP6K2 protein to bind to the other polypeptide.

Still another aspect of the invention is a method of determining the quantity of human HSP90 protein which binds to human IP6K2 protein, or of human IP6K2 protein which binds to human HSP90 protein. A first protein is contacted with a second protein. The first protein is human IP6K2 protein and the second protein is human HSP90 protein or the first protein is human HSP90 protein and the second protein is human IP6K2 protein. The quantity of the first protein which is bound to the second protein is determined.

According to another embodiment of the invention a fusion protein consisting of a first polypeptide and a second polypeptide are provided. The second polypeptide is a portion of a mammalian IP6K2 protein, which is sufficient to bind to HSP90 protein. The first polypeptide is not a portion of a mammalian IP6K2 protein.

Another embodiment of the invention is a device for screening for candidate pro-apoptotic drugs. The device comprises a solid surface to which one of a first and a second polypeptide has been affixed. The first and said second polypeptides comprise at least a portion of the complete sequence of amino acids of HSP90 protein and IP6K2 protein, respectively. Each of said polypeptides contains a sufficient portion of HSP90 protein or IP6K2 protein to bind to the other polypeptide.

Still another embodiment of the invention is a kit for screening test compounds for candidate pro-apoptotic drugs. Components of the kit include a solid surface to which one of a first and a second polypeptide has been affixed; the first and said second polypeptides comprise at least a portion of the complete sequence of amino acids of HSP90 protein and IP6K2 protein, respectively. Each of said polypeptides contains a sufficient portion of HSP90 protein or IP6K2 protein to bind to the other polypeptide. The kit also includes a container comprising unbound protein which is not affixed to the solid surface. If an HSP90 polypeptide is affixed to the solid surface then the unbound protein is an IP6K2 polypeptide, and if the IP6K2 polypeptide is affixed to the solid surface then the unbound protein is an HSP90 polypeptide.

These and other embodiments which will be apparent to those of skill in the art upon reading the specification provide the art with tools for identifying and developing new candidate drugs for treating cancer.

BRIEF DESCRIPTION OF THE DRAWINGS

FIG. 1A-1F. Inositol Hexakisphosphate Kinase-2 (IP6K2) binds HSP90. FIG. 1A. IP6K2 contains a motif resembling p23, a cochaperone of HSP90. FIG. 1B. Co-immunoprecipitation of endogenous HSP90 by overexpressed myc-tagged IP6K2 and IP6K3 in HEK 293 cells. HEK 293 cells were transfected with pCMV-myc vector containing any of the three IP6K clones (IP6K1/K2/K3). Protein (1 mg) from each cell lysate was immunoprecipitated by anti-myc antibody. Samples run on 4-12% SDS-PAGE, were immunoblotted with monoclonal HSP90 antibody. Lane 1 shows the untransfected control. IP6K2 and IP6K3 bind robustly to HSP90 but IP6K1 does not. The membrane was also blotted with anti-myc antibody to monitor the concentration of immunoprecipated IP6K isoforms. FIG. 1C. Co-immunoprecipitation of myc-IP6K2 by endogenous HSP90 from HeLa cells. Endogenous HSP90 was immunoprecipitated using a monoclonal antibody from cells with and without overexpressing myc-IP6K2. Co-immunoprecipitated myc-IP6K2 was checked by immunoblotting with anti-myc antibody. HSP90 levels were also confirmed by western blotting. FIG. 1D. Co-immunoprecipitation of endogenous IP6K2 by endogenous HSP90 in mouse brain. Protein (3 mg) from brain extract was immunoprecipitated for each experiment with no antibody (lane 1), general IgG (lane 2) or HSP90 monoclonal antibody (lane 3). Co-immunoprecipitated endogenous IP6K2 was detected by blotting with IP6K2 specific polyclonal antibody. FIG. 1E. Direct binding of immunoprecipitated myc-K2 with exogenously added HSP90 purified from HeLa cells (lane 2). Myc-vector transfected HeLa cells were used as negative control (lane 1). FIG. 1F. Endogenous HSP90 does not coprecipitate with mutants of IP6K2 in the putative HSP90 binding region. R133A, R136A and E138-9A no longer bind whereas W131A has little effect on binding.

FIG. 2A. HSP90 overexpression leads to decreased IP6K activity in vivo. HeLa and HEK 293 cells (either untransfected or transfected with myc-IP6K2, HA-HSP90 or both) were labeled with [$^3$H]inositol and inositol phosphates were isolated by HPLC. IP7 formed by IP6K in the cells was calculated based on IP7 (product) over IP6 (substrate) and was considered as reflection of IP6K activity in vivo. IP6K activity in the untransfected cells was considered to be 100%. FIG. 2B. HSP90 fails to inhibit IP7 formation in vivo by IP6K2 mutants that can not bind HSP90. [$^3$H]inositol labeled IP7 was assessed in HeLa cells co-transfected with myc-IP6K2 (WT or the mutants) and HA-HSP90. R133A and R136A mutants of IP6K2 display more activity than wild type and are not inhibited by HSP90. The low activity of the catalytically deficient W131A mutant is further depressed by HSP90 overexpression. FIG. 2C. IP6K activity in vitro of WT and mutant IP6K2 in absence and presence of purified HSP90 from HeLa cells. Catalytic activity of the WT enzyme is significantly reduced after addition of HSP90 whereas the R133A and R136A mutants are equally active as the even in the presence of HSP90. W131A mutant lost 80% of catalytic activity as compared to the WT or the other two active mutants. FIG. 2D. Deficient IP6 binding of catalytically inactive IP6K2 W131A mutant. [$^3$H]IP6 binding is reduced 50% in the IP6K2 W131A mutant establishing a role for W131A in substrate binding and catalytic activity. Substrate binding of IP6K2 R133A and IP6K2 R136A mutant is the same as in WT samples. FIG. 2E. In vitro binding of purified endogenous HSP90 to immunoprecipitated myc IP6K2 is abolished in presence of IP6. After preincubation of IP6K2 with increasing concentrations of IP6 for 15 min. in binding buffer (20 mM Tris 7.4, 1 mM DTT, 1 mM PMSF and protease inhibitor cocktail), HSP90 was added and incubated for 1 h. The beads were washed three times with binding buffer and bound HSP90 was analyzed by blotting with anti-HSP90 monoclonal antibody. Amount of immunoprecipitated myc IP6K2 was also checked by western blotting with anti-myc antibody and found to be equal in all the samples (data not shown). FIG. 2F. IP6K activity in vivo is increased in the absence of endogenous HSP90. HSP90 was depleted using siRNA in [$^3$H] inositol labeled HeLa cells and inositol phosphates separated by HPLC. FIG. 2G. IP6K activity in WT and HSP mutant Yeasts in vivo. IP6 and IP7 were monitored following [$^3$H] inositol labeling of intact cells. HSC82 mutant displays a 2.5 fold increase in IP6K activity whereas in HSP104 mutant IP6K activity is slightly decreased.

FIG. 3A, 3B, 3C. IP6K2-HSP90 interaction is disrupted by HSP90 inhibiting drugs. Drug treatment and coimmunoprecipitation of endogenous HSP90 from myc-IP6K2-transfected HeLa cells were done as described. Cisplatin (CP-30 overnight, FIG. 3A), novobiocin (NB-500 µM, overnight, FIG. 3A) and staurosporine (ST-1 µM, 6 h, FIG. 3B) disrupt the binding of HSP90 with IP6K2, whereas AAG (1 µM, overnight, FIG. 3C) augments binding. FIG. 3D: in vitro binding of HSP90-1P6K2 in presence of various concentrations of drugs. Purified (250 nM) endogenous HSP90 (from HeLa) was incubated with indicated concentrations of various drugs at 37° C. for 30 min. in binding buffer (20 mM Tris 7.4, 1 mM DTT, 1 mM PMSF and protease inhibitor cocktail). The complex was added to purified myc-IP6K2 (immunoprecipitated from HEK 293 cells) and was incubated for 30 min. at 37° C. The beads were washed three times with binding buffer and bound HSP90 was analyzed by blotting with anti-HSP90 monoclonal antibody. FIG. 3E. Drugs that disrupt IP6K2-HSP90 binding enhance IP7 generation in vivo. Cells were labeled with [$^3$H]inositol for 3 days. After drug treatment, as in FIG. 3A-3C, IP6K activity in vivo was measured by resolving [$^3$H]inositol phosphates by HPLC and calculating IP7/IP6 ratio. IP6K activity in the control was considered as 100%. CP, NB and ST increase IP6K activity, whereas AAG diminishes IP6K activity both in untransfected and K2 transfected cells.

FIG. 4A. Differential effects of novobiocin and AAG on intracellular localization of myc-IP6K2. Following drug treatment, nuclei were isolated from the rest of the cytoplasm. In each lane, 60 µg of total protein was loaded and the localization of IP6K2 assessed with an anti-myc antibody. Bands were analyzed by densitometry and changes in localization were calculated with the basal distribution of IP6K2 as a control. Novobiocin increases nuclear and decreases cytosolic IP6K2 whereas AAG elicits the opposite effect. FIG. 4B. GFP-IP6K2 stably expressed in HEK 293 cells is distributed to a similar extent in cytosol and nucleus. Cells were stained with Hoechst stain for nucleus. FIG. 4C. Overexpression of pDSRed-HSP90 in HEK293 stably expressing GFP-IP6K2 retains IP6K2 completely in the cytosol. HSP90 also co-localizes well with IP6K2 as indicated by the yellow color of the merged picture. FIG. 4D. IP6K2 is translocated to the nucleus after novobiocin treatment. GFP-IP6K2 stable HEK 293 cells were treated with novobiocin for 3 h. FIG. 4E. HSP90 reverses novobiocin induced nuclear localization of IP6K2. GFP-IP6K2 expressing stable HEK 293 cells were transfected with pDSRed-HSP90 and were treated with novobiocin for 3 h. Cells overexpressing HSP90 (arrow a) display co-localization of IP6K2-HSP90 in the cytosol, whereas in cells lacking overexpressed HSP90 (arrow b), IP6K2 is nuclear. FIG. 4F. Effects of HSP90 depletion on intracellular localization of IP6K2. In HeLa, cells transiently expressed GFP-IP6K2 occurs diffusely throughout cells. Depletion of HSP90 by RNAi (depletion is 100% as shown in FIG. 6), leads to nuclear accumulation of IP6K2.

FIG. 5A. IP6K2 mutants deficient in HSP90 binding display markedly augmented cell death. Seventy-two hours after transfection, apoptotic nuclei were counted in 250 cells and the percentage of dead cells were calculated. Expression profiles of wild type and mutant IP6K2 assessed by western blotting are the same (data not shown). Cell death prevention by HSP90 overexpression with IP6K2wt was not evident for IP6K2 mutants deficient in HSP90 binding. FIG. 5B. Caspase 3 activity is increased in cells transfected with mutant active IP6K2 which do not bind HSP90. Activity was measured 72 h after transfection. Percent increase was determined by considering $OD_{405}$ of control sample as 100%. Data are means of three independent experiments. FIG. 5C. Decrease in cell survival by cisplatin, novobiocin and staurosporine involves IP6K2 as measured by MTT assay. Transfection of IP6K2wt but not the W131A mutant reduces survival by these drugs in HeLa cells. By contrast, AAG induced decrease in survival is unaffected by IP6K2 transfection. FIG. 5D. HSP90 overexpression reverses IP6K2 mediated decrease in cell survival after cisplatin (30 µM) treatment. Cell death was elicited by addition of cisplatin to either untransfected, or transfected (HA-HSP90 alone, myc-IP6K2 alone and both) HeLa cells for the indicated time period and survival rate was measured by MTT assay. FIG. 5E. Cisplatin and novobiocin induced cell death involves IP6K2. Cell death (measured by % apoptotic nuclei detection) in drug treated HeLa cells is diminished by IP6K2 depletion. AAG induced cell death is unaffected by K2 knockdown. FIG. 5F. HSP90 depletion augments IP6K2 elicited cell death in HeLa cells. Cell death elicited by IP6K2 significantly increases in the absence of HSP90.

(FIG. 8A). Mapping of HSP90 to identify the IP6K2 binding region. Fragments 1-272 (N-terminus, N), 273-732 (Middle and C-terminus, MC) and 629-732 (C-terminus, C) were generated and cloned into pGEX vector and bacterially purified. (FIG. 8B.) Determination of binding region of HSP90 to IP6K2 by in vitro binding. 250 nM of various purified HSP90 WT and deletion constructs were incubated for 30 min. at 37° C. with purified myc-IP6K2 (immunoprecipitated from HEK 293 cells). The beads were washed three times with binding buffer and bound HSP90 was analyzed by blotting with anti-HSP90 monoclonal antibody. HSP90's binding site for IP6K2 was found to be in the C-terminus region.

FIG. 9A. IP6K2 mutants that do not bind to HSP90 are localized more in the nucleus as compared to wild type IP6K2. GFP-tagged proteins were expressed and localization was observed by immunofluorescence. FIG. 9B. GFP-IP6K2 with mutation in the nuclear localization signal (K2iNLS) fails to translocate to the nucleus of HeLa cells following novobiocin treatment (lower panel), whereas the wild type enzyme displays nuclear translocation (upper panel).

FIGS. 10A-10B. FIG. 10A: Western blotting to confirm knockdown of IP6K2 by siRNA. β-tubulin was run as control FIG. 10B: Densitometric scanning of the bands in FIG. 10A to quantify the percentage decrease in endogenous IP6K2 expression after siRNA treatment. FIG. 10C. IP6K activity is decreased after K2 knockdown. [$^3$H]inositol labeled HeLa cells were transfected with siRNA of control or IPGK2 for 48 h and the inositol phosphate profile was monitored by HPLC. IP6K activity was calculated as IP7/IP6. A decrease of 40% decrease was observed in total IP6K activity in vivo after knockdown of IP6K2. FIG. 10C. IP6K activity is decreased after K2 knockdown. [$^3$H]inositol labeled HeLa cells were transfected with siRNA of control or IP6K2 for 48 h and the inositol phosphate profile was monitored by HPLC. IP6K activity was calculated as IP6/IP6. A 40% decrease was observed in total IP6K activity in vivo after knockdown of IP6K2.

DETAILED DESCRIPTION OF THE INVENTION

Figure 2A:
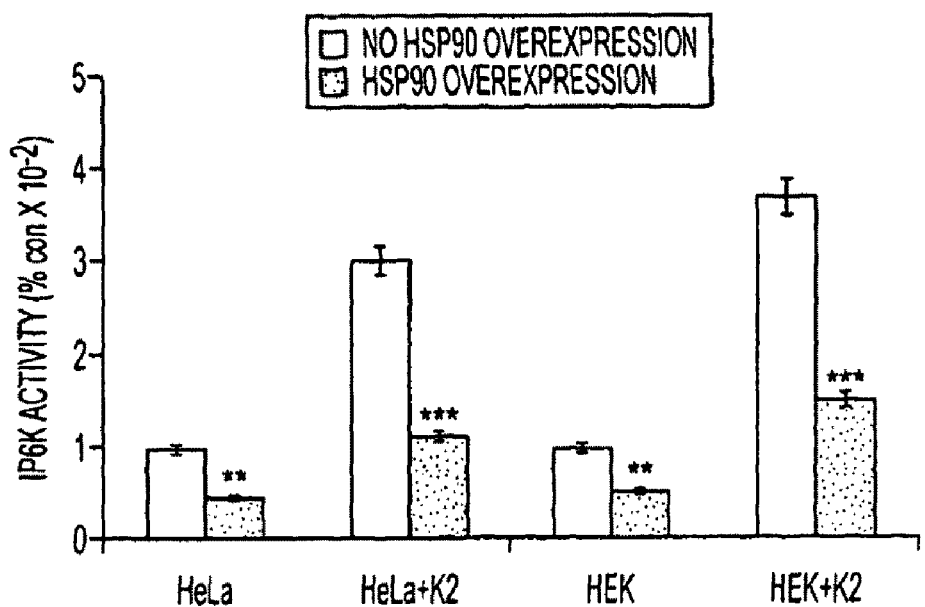
FIG. 2A-2G Regulation of IP6K2 activity by HSP90.

The inventors have discovered that anti-apoptotic actions of HSP90 are mediated through IP6K2 inhibition. HSP90 binds a heretofore unrecognized p23-like motif in IP6K2 to inhibit IP7 generation and thus promote cell survival. Anti-cancer drugs and selective mutations which block HSP90-IPGK2 binding augment IP7 production and cell death.

Interactions of IP6K2 and HSP90 physiologically regulate cell survival. Selective disruption of binding substantially augments IP7 generation and cell death. Moreover, the anti-apoptotic actions of HSP90 are abolished by IP6K2 mutants that do not bind HSP90. Thus, the antiapoptotic, cancer promoting actions of HSP90 may reflect its inhibition of IP6K2's apoptotic influences. Several anti-cancer drugs exert their cytotoxic effects, at least in part, by disrupting IP6K2-HSP90 binding. Of the four anti-cancer drugs we have examined, three of them, cisplatin, novobiocin and staurosporine, disrupt HSP90-IP6K2 binding and enhance IP7 formation. The fourth, 17-aminoallyl geldanamycin(AAG), augments the binding and decreases IP7 levels. AAG, like other geldanamycin derivatives, binds to the N-terminus of HSP90, whereas IP6K2 binds to the C-terminus. Binding of ATP or AAG to the N-terminus is reported to expose the C-terminus to interactions with various proteins (35). Presumably the increased IP6K2 binding elicited by AAG reflects such an allosteric action which probably does not play a role in the apoptotic actions of AAG.

By contrast, the augmented IP7 formation following disruption of IP6K2-HSP90 binding elicited by cisplatin, novobiocin and staurosporine appears to contribute to the cytotoxicity of these drugs. Other actions of these three agents vary, cisplatin damaging DNA, novobiocin inhibiting topoisomerase II, and staurosporine inhibiting protein kinase C, cyclic AMP dependent kinase and Akt by competing at the ATP binding sites (36, 37). Cisplatin has been reported to bind to the C-terminus of HSP90, decreasing the transcriptional activity of androgen and glucocorticoid receptors while not affecting other HSP regulated proteins such as the phosphokinases Raf-1, Lck, and c-Src (29). Novobiocin binds to the C-terminus of HSP90 and can allosterically interfere with the binding to its N-terminus of proteins such as mutant p53 and Raf-1 (28). It is difficult to ascertain the extent to which apoptotic actions of drugs are attributable to one or another mechanism. Nonetheless, the major reduction of cell death elicited by novobiocin, cisplatin and staurosporine in cells depleted of IP6K2 implies that activation of IP7 formation by disruption of IP6K2-HSP90 binding is a major cytotoxic mechanism for these drugs. The failure of IP6K2 depletion to influence cell death elicited by AAG fits with the failure of this drug to disrupt IP6K2-HSP90 binding and augment IP7 formation.

Our findings have therapeutic relevance. One could readily screen for agents that selectively block IP6K2-HSP90 binding. Such substances would be predicted to have therapeutic effects in cancer and may elicit fewer side effects than classical chemotherapeutic agents that act by mechanisms such as DNA damage. Inhibitors of HSP90-IP6K2 binding may also be more selective and less toxic than drugs that affect HSP90's ATPase activity, which may exert more global influences.

Exemplary amino acid sequences which can be used according to the invention are shown in the accompanying sequence listing. The sequences are only exemplary. See for example, HSP90 alpha (SEQ ID NO: 2 and 3)and beta (SEQ ID NO: 4), and IP6K2 (SEQ ID NO: 1). Other allelic variants and isoforms from humans can be used. Other mammalian species corresponding amino acids can be used. These are well within the skill of the art for these known proteins.

The screening methods of the present invention all rely on the principle of interference in the binding of IP6K2 and HSP90 by a compound. Thus any assay format for measuring protein-protein interactions that is known in the art can profitably be used. For example, both in vitro and in vivo tests can be used. One of the proteins can be immobilized, for example, on a microtiter dish, or on a column packing matrix. Immobilization can be direct or indirect, e.g., through a domain of a fused protein. Assays can employ radiolabels, enzyme assays, antibodies, florescent labels, colorimetric, and/or growth assays. Binding interactions can be assessed by measuring the bound or the unbound fraction. Any phenomenon associated with the binding or inhibition can also be monitored, including cell death, subcellular localization, catalytic activity of IP6K2, and IP7 formation.

According to some embodiments of the invention, the entire IP6K2 or HSP90 is used, as is, or fused to another polypeptide domain or protein. Alternatively, polypeptide portions of either IP6K2 or HSP90 can be used, so long as they contain the portions of IP6K2 and HSP90 which are required for binding to each other. Suitable portions of human HSP90 for use include amino acids 751-854 of SEQ ID NO: 2 and 630-731 of SEQ ID NO: 3. Suitable portions of IP6K2 for use include amino acids 131-140.

In vivo assays such as the GAL4 based assays described by Fields et al. (*Nature* 340, 245-46, 1989) can be used. Such assays employ fusion proteins of the two interacting proteins of interest. One partner is fused to an activation domain and one partner is fused to a DNA binding domain. Neither domain by itself will activate transcription of a suitable reporter gene. However, when the two domains are brought into proximity, such as by the interaction of the two interacting proteins, then the reporter's transcription is activated. Other suitable systems have been developed. Spencer et al. *Science,* 262, 1019-1024 (1993) developed a system which relies on the interaction of FKBP12 and FK1012. Fearon et al., *Proc. Natl. Acad. Sci. USA,* 89,7958-7962 (1992) teaches a system which is based on yeast GAL4 but which can be used in mammalian cells. Reporter genes which are used are preferably those whose expression can be quantitatively or semi-quantitatively assayed, including drug resistance enzymes and anabolic enzymes. Both the his3 and the β-galactosidase genes can be used to advantage. Candidates which are identified as having inhibitory activity in such assays can be further tested in an animal to determine if the candidate drug induces apoptosis.

In vivo assays may be preferable to in vitro assays because they require that the compound being tested penetrate the cells and locate the appropriate target proteins. However, both types of methods may be used, either individually or sequentially.

Candidate drugs are identified as those which inhibit the binding of IP6K2 to HSP90. Such inhibitory molecules can be identified by screening for interference of the IP6K2/HSP90 interaction where one of the binding partners is bound to a solid support and the other partner is labeled. Antibodies specific for epitopes on IP6K2 or HSP90 which are involved in the binding interaction will interfere with such binding. Solid supports which may be used include any polymers which are known to bind proteins. The support may be in the form of a filter, column packing matrix, beads, microtiter dish, chip, and the like. Labeling of proteins can be accomplished according to any technique known in the art. Radiolabels, enzymatic labels, and fluorescent labels can be used advantageously. Alternatively, both IP6K2 and HSP90 may be in solution and bound molecules separated from unbound subsequently. Any separation technique known in the art may be employed, including immunoprecipitation or immunoaffinity separation with an antibody specific for the unlabeled binding partner.

The binding of IP6K2 and HSP90 can be quantitatively evaluated in the absence of test compounds. Such assays can be used to determine if a biological sample contains a mutant IP6K2 or HSP90 protein. Such assays can also be used to determine if a particular tissue expresses IP6K2 or HSP.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

HSP90 and IP6K2 Co-Precipitate

We wondered whether the rapid activation of IP6K2 in response to apoptotic stimuli reflects interaction with other proteins. Recently we developed a Gestalt Domain Detection Algorithm (GDDA) facilitating the identification of protein-protein recognition motifs (23, 24). GDDA analysis reveals a sequence in IP6K2 (amino acids 131-140) which resembles a highly conserved motif in p23, a co-chaperone which binds HSP90 with high affinity (25) (FIG. 1a). This sequence is closely similar in IP6K2 and IP6K3 but not IP6K1. Fitting with this sequence analysis, we find that endogenous HSP90 co-precipitates with Myc-IP6K2 and IP6K3 but not IP6K 1 (FIG. 1b). Endogenous HSP90 in HeLa cells binds to overexpressed Myc-IP6K2 (FIG. 1c). Endogenous HSP90 and endogenous IP6K2 also co-precipitate from mouse brain (FIG. 1d). Binding of purified mammalian HSP90 to immunoprecipitated Myc-IP6K2 confirms that the interaction is direct (FIG. 1e).

Example 2

HSP90 Inhibits Catalytic Activity of IP6K2

Figure 2B:
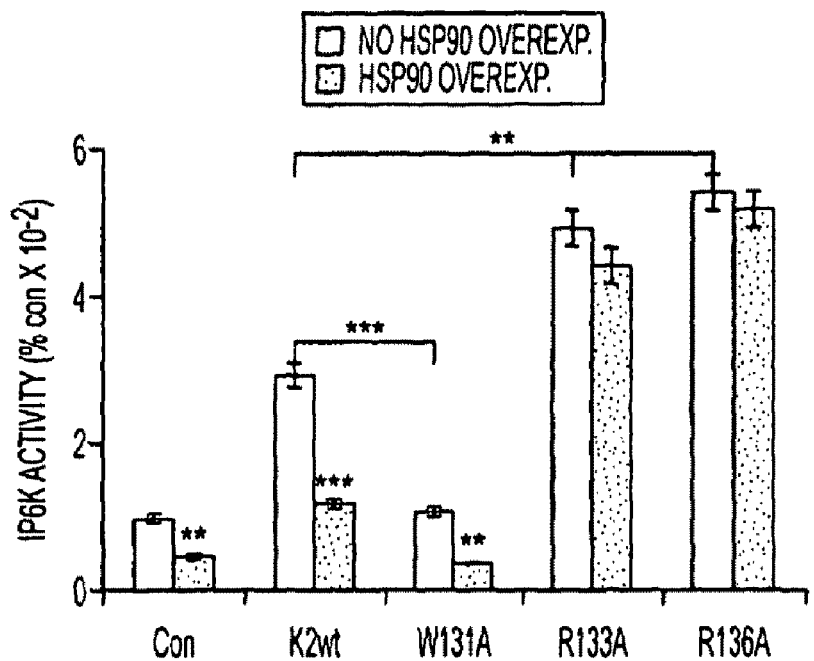
Figure 2C:
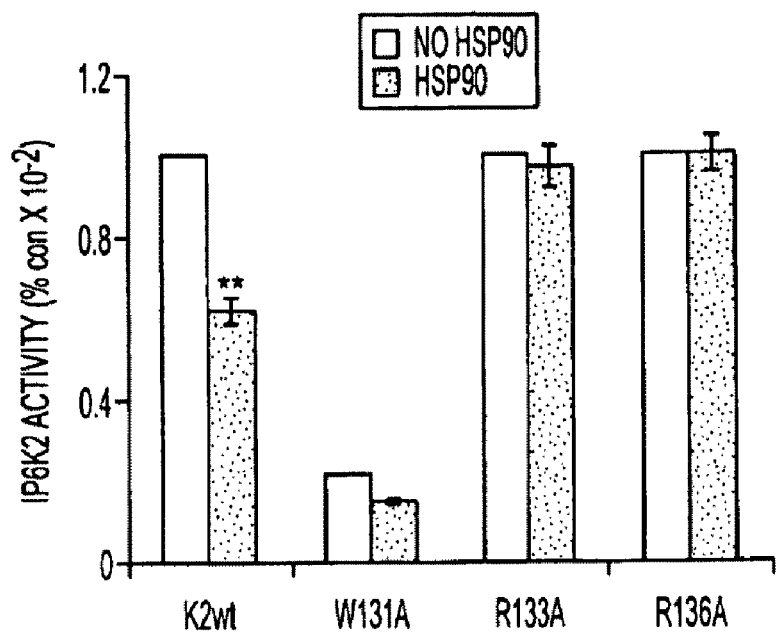
Figure 2D:
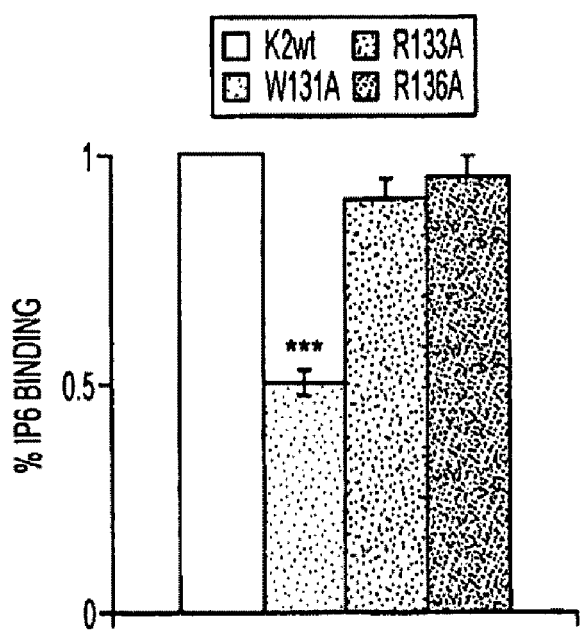
Figure 2E:
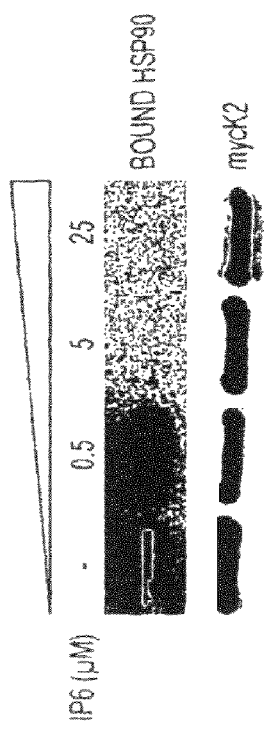
Figure 2G:
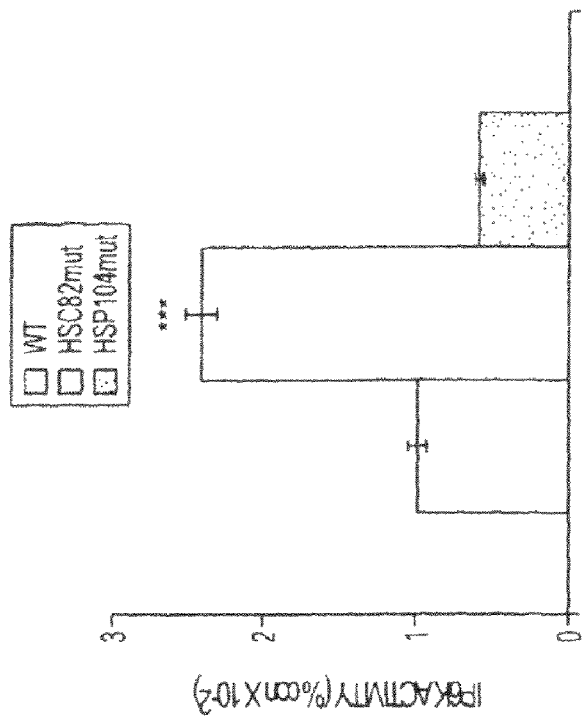
Figure 2F:
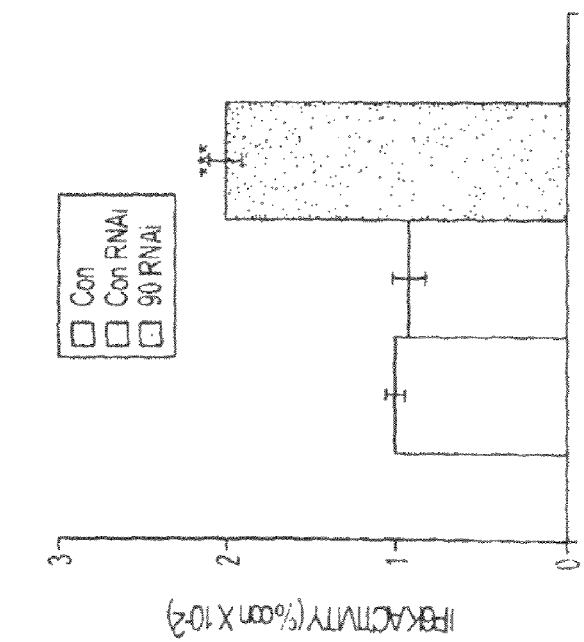

To ascertain whether HSP90 binding to IP6K2 regulates IP6K activity in vivo, we labeled HeLa and HEK293 cells with [$^3$H]inositol and monitored conversion of IP6 to IP7. In both cell lines overexpression of HSP90 diminishes by about half the activity of IP6K in untransfected cells as well as in cells transfected with IP6K2 (FIG. 2a). Conversely, depletion of HSP90 by RNA interference (FIG. 5) augments IP6K activity (FIG. 2b). These findings suggest that HSP90 binding to IP6K2 physiologically inhibits catalytic activity of the enzyme. We explored the possibility that IP6K activity is similarly regulated in yeast. Yeast HSC82 resembles human HSP90 both in amino acid sequence and in its presence under basal conditions (26, 27). Deletion of HSC82 elicits a doubling of IP7 formation whereas deletion of an unrelated HSP, HSP104, does not, instead slightly diminishing IP7 formation (FIG. 2c).

Example 3

Binding Domain in IP6K2 Identified

Figure 3A:
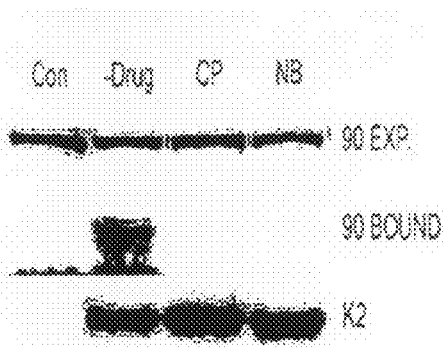
FIG. 3A-3E Cisplatin, novobiocin and staurosporine block HSP90-IP6K2 interaction and increase IP6K2 activity in cells.
Figure 3B:
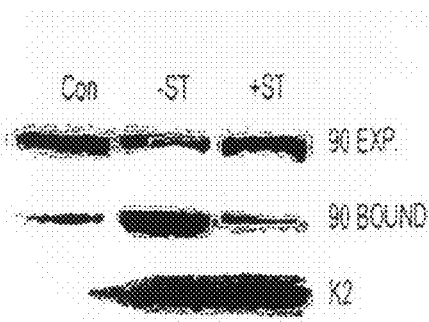
Figure 3C:
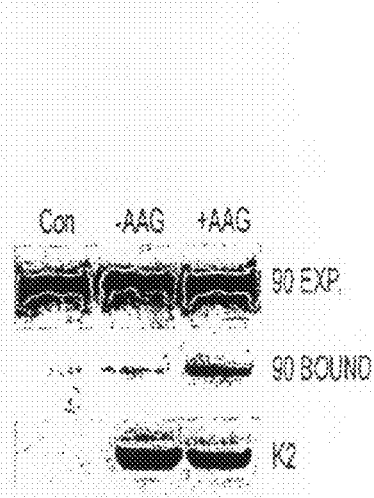

We mapped the HSP90 binding domain of IP6K2 with mutations in its putative HSP90 binding motif. Mutation of tryptophan-131 modestly diminishes IP6K2-HSP90 binding, while mutations of arginine-133, arginine-136 or glutamates-138,139 abolish binding (FIG. 3a). IP6K2-W131A displays greatly reduced IP6K catalytic activity (FIG. 3b) which appears to reflect diminished binding of its substrate IP6 (FIG. 3c), whereas IP6K2-R133A and IP6K2-E138-9A have the same catalytic activity and IP6 binding as IP6K2wt (FIGS. 3b and 3c).

Example 4

HSP90 Binding to IP6K2 Attenuates Cell Death

Figure 3D:
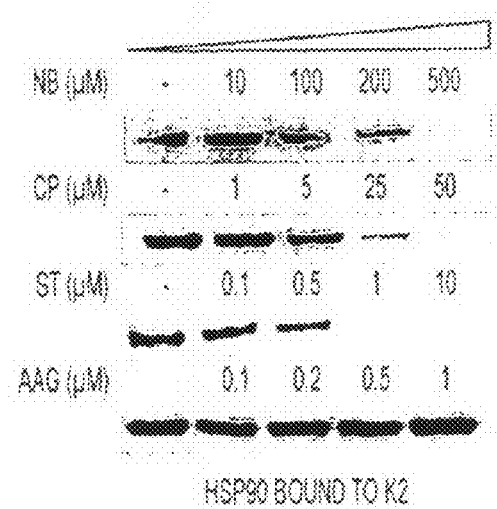
Figure 3E:
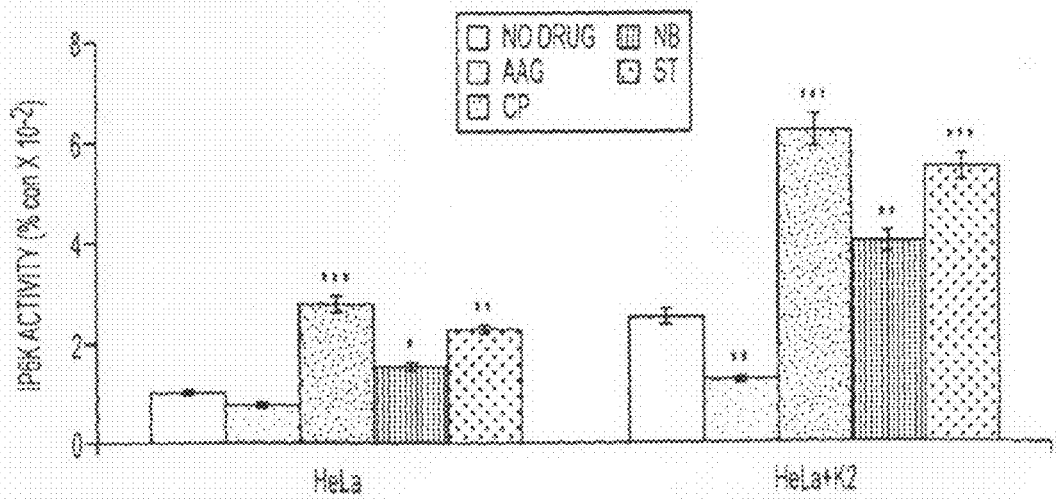

We next examined the influence of these mutations on IP6K2 activity in vivo (FIG. 3d). Consistent with the loss of catalytic activity in IP6K2-W131A in vitro, cells transfected with this mutant display much less enzyme activity than IP6K2wt. By contrast, cells overexpressing IP6K2-R133A or IP6K2-E138-9A, which cannot bind HSP90, have almost twice the enzyme activity of cells with IP6K2wt. Whereas overexpression of HSP90 markedly reduces IP7 formation in cells with IP6K2wt, no reduction in IP7 formation occurs in cells overexpressing R133A or E138-9A mutants. Thus, the binding of HSP90 to IP6K2 physiologically downregulates IP7 formation. To determine whether HSP90-IP6K2 binding regulates IP7-associated cell death we transfected HeLa cells with IP6K2wt or mutants (FIG. 3e). Overexpression of wild type IP6K2 modestly augments cell death, an effect which is reversed when HSP90 is also co-expressed. Strikingly, cell death following overexpression of the RI33A and E138-9A mutants of IP6K2 is five-fold greater than with wild type IP6K2 overexpression and HSP90 fails to reduce cell death. Thus, the binding of endogenous HSP90 to IP6K2 physiologically attenuates its apoptotic actions. This conclusion is supported by the failure of HSP90 overexpression to reduce the cell death elicited by the R133A and E138-9A mutants that cannot bind HSP90. The importance of IP6K2 catalytic activity for cell death is illustrated by the absence of cell death augmentation following overexpression of the catalytically deficient IP6K2 W131A mutant.

Example 5

Apoptotic Potency of Drugs Correlates with Inhibition of Binding of IP6K2-HSP90

Figure 4A:
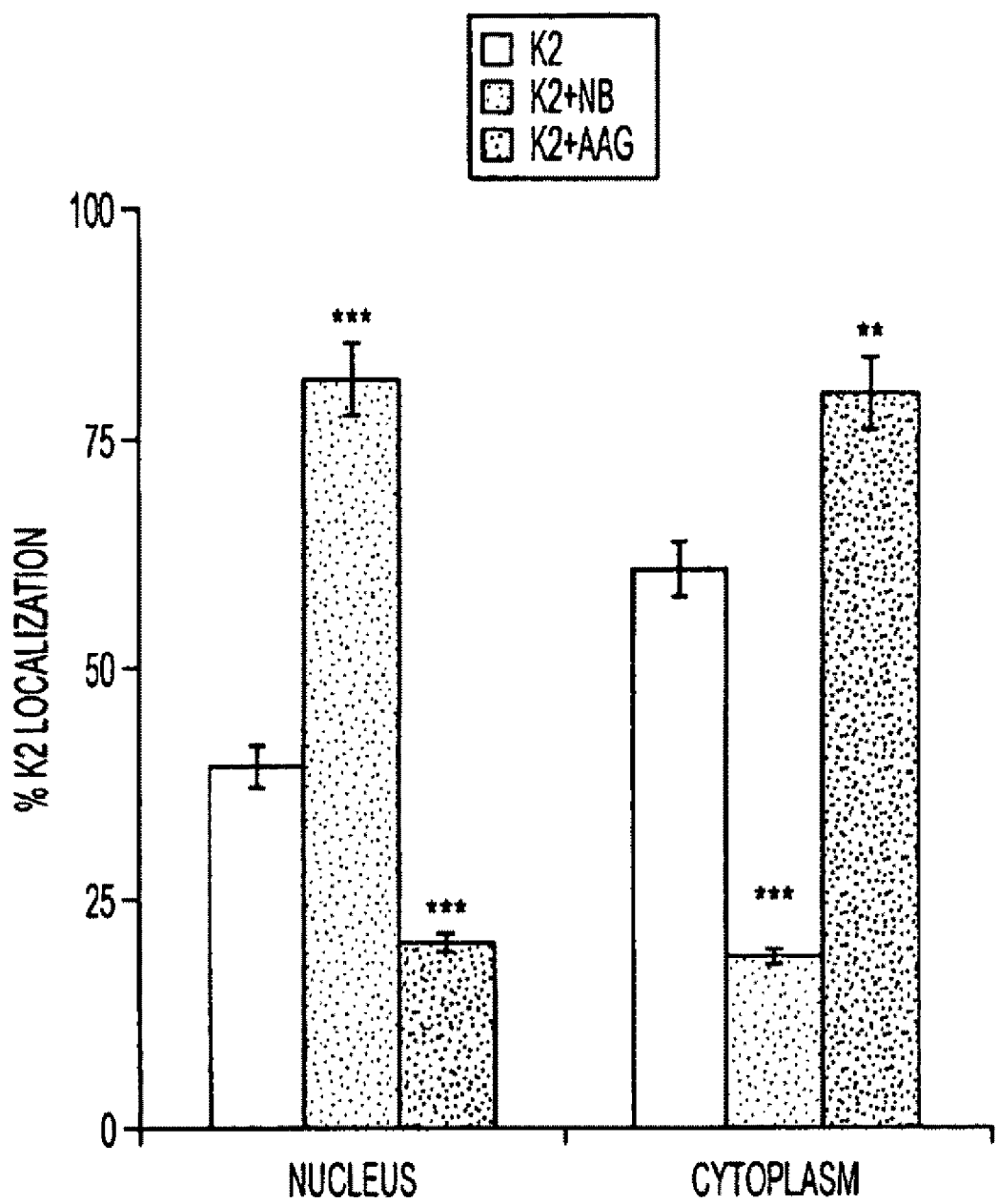
FIG. 4A-4F. HSP90 regulates intracellular localization of IP6K2.
Figure 4B:
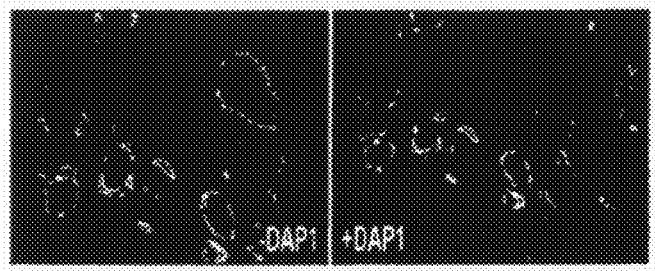
Figure 4C:
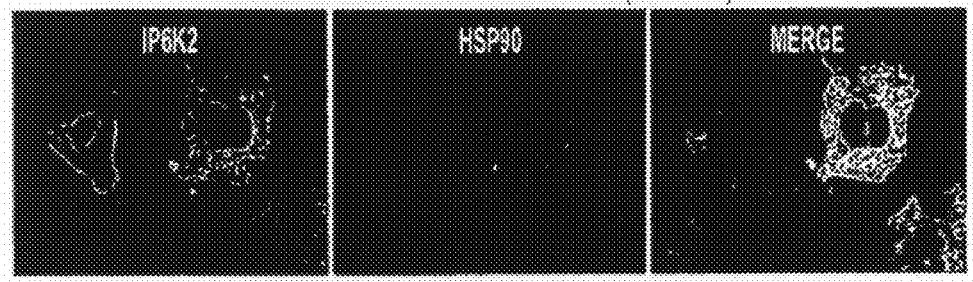

A number of apoptosis-inducing anti-cancer drugs act, at least in part, by binding to HSP90. Such drugs include the geldanamycin derivative AAG (17-aminoallyl geldanamycin), novobiocin, and cisplatin (18-22, 28-30). We wondered whether the apoptotic actions of these and other drugs involve HSP90-IP6K2 interactions. In coimmunoprecipitation experiments in HEK 293 cells, cisplatin, novobiocin and staurosporine diminish IP6K2-HSP90 binding while AAG augments this binding (FIG. 4a). We established that the drugs directly block IP6K2-HSP90 and assessed their relative potencies in experiments using the purified proteins (FIG. 4b). Novobiocin, cisplatin and staurosporine reduce binding by 50% at concentrations of about 200 µM, 1-5 µM and 0.1 µM respectively. These potencies fit well with the apoptotic potencies of the drugs in cell culture (10, 28, 31, 32). Similar to results in intact cells, AAG fails to inhibit binding in vitro. Staurosporine has not previously been reported to bind to HSP90. We examined its influence on HSP90 binding to ATP-agarose beads and observe 50% reduction of binding at about 0.2 µM similar to the drug's potency in disrupting IP6K2-HSP90 binding and consistent with its direct binding to HSP90 (data not shown). Disruption of the binding impacts IP6K2 activity. Thus, in HeLa cells with or without overexpression of IP6K2, cisplatin, novobiocin and staurosporine elicit augmented IP6K2 activity, while AAG, which increases IP6K2-HSP90 binding, is associated with less IP7 formation (FIG. 4c). Blockade by drugs of IP6K2-HSP90 binding presumably accounts for their enhancement of IP7 generation (10). We obtain essentially the same results in HEK293 cells (data not shown).

Example 6

Binding Domain on HSP90 Identified

Figure 6:
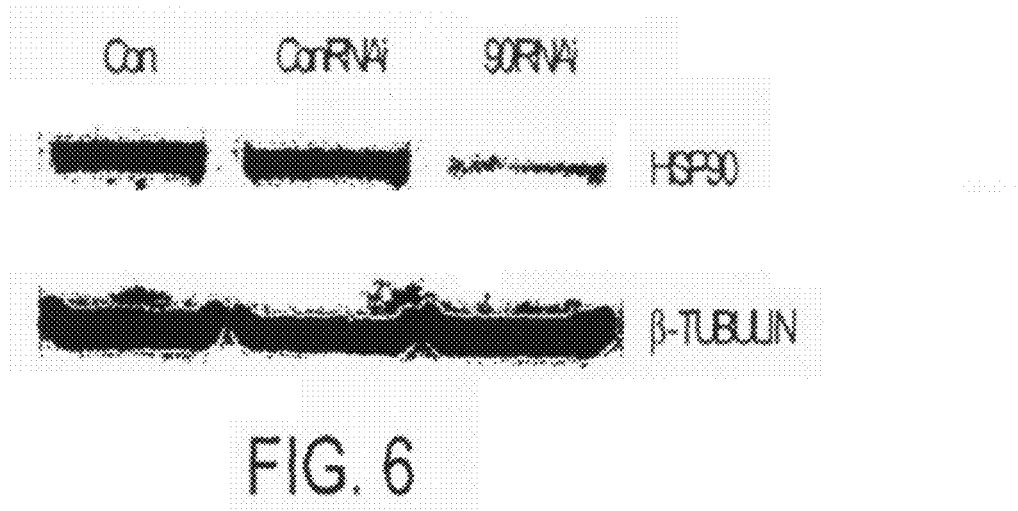
FIG. 6: RNAi experiment to deplete HSP90 in HeLa Cells. HeLa cells were grown in a 6-well plate to 50% confluency and transfected with 50 nM of HSP90 siRNA for 48 h. Cells were lysed, 50 µg of total protein was loaded onto 4-12% SDS-PAGE and western blotted with an HSP90 monoclonal antibody.

IP6K2 binds to HSP90's C-terminus (FIGS. 6a and 6b) which accords with the disruption of IP6K2-HSP90 binding by drugs like cisplatin and novobiocin which also bind to the C-terminus of the chaperone. By contrast, p23 which primarily binds to HSP90's N-terminus (33) only influences in vitro IP6K2-HSP90 binding at a high molar ratio (1:20) and does not affect their coprecipitation in HeLa cells (data not shown).

Example 7

Known Anti-Cancer Drugs Block IP6K2-HSP90 Binding

Figure 4D:
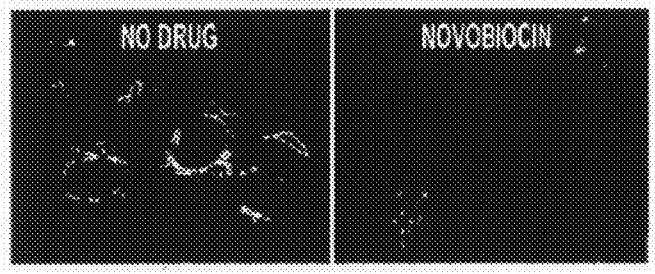
Figure 4E:
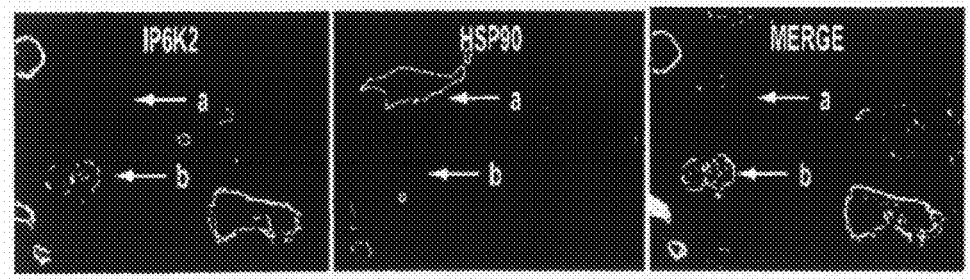
Figure 7:
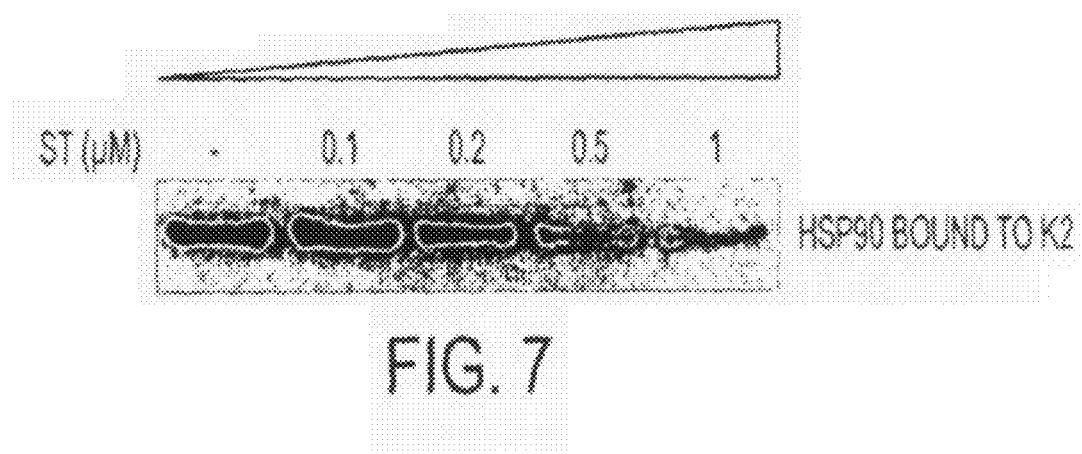
FIG. 7: Staurosporine inhibits binding of HSP90 to ATP-agarose beads in a concentration dependent manner. Purified HSP90 was pre-incubated with increasing concentrations of staurosporine for 10 minutes on ice and then incubated with immunoprecipitated bead bound myc-IP6K2 at 37° C. for 1 hour. Beads were washed with wash buffer and run on 4-12% SDS-PAGE. Bound HSP90 was detected by western blotting with anti-HSP90 monoclonal antibody.
Figure 8A:
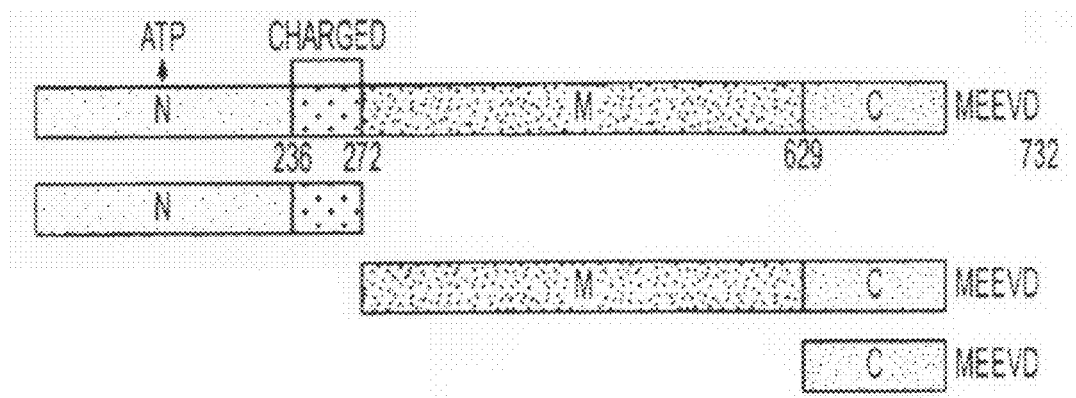
FIGS. 8A-8B.
Figure 8B:
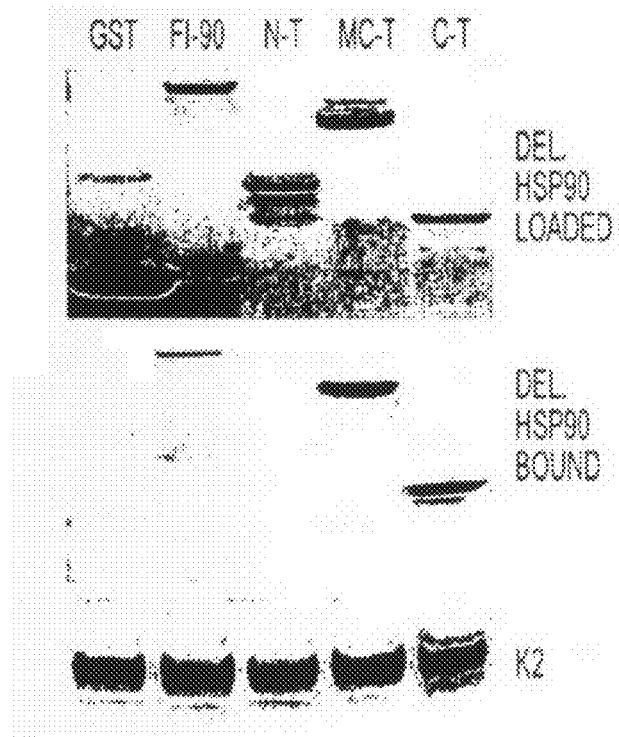

We wondered whether the apoptotic actions of these drugs are attributable to disruption of IP6K2-HSP90 binding. Accordingly, we examined whether IP6K2 overexpression alters the apoptotic effects of these drugs (FIG. 4d). Apoptotic actions of cisplatin, novobiocin, and staurosporine are markedly enhanced by IP6K2 overexpression, while cell death following AAG is unaffected by IP6K2 overexpression. To explore further the role of IP6K2 in drug mediated cytotoxicity, we depleted IP6K2 in HeLa cells by RNA interference which results in ~40% less IP7 formation in vivo (FIGS. 7a and 3b). Cell death elicited by novobiocin and cisplatin is reduced by almost half in IP6K2 depleted cells, while the apoptotic actions of AAG are unaffected by IP6K2 depletion (FIG. 4e). We previously reported that IP6K2 depletion prevents the apoptotic effects of staurosporine (10). The substantial blockade of drug killing by partial depletion of IP6K2 as well as its augmentation by overexpression of IP6K2 indicate that cisplatin, novobiocin and staurosporine, which block IP6K2-HSP90 binding, kill cells in significant part by disruption of this binding whereas AAG, which does not affect the binding, acts differently.

Example 8

HSP90 RNAi Increases Cell Death

Figure 4F:
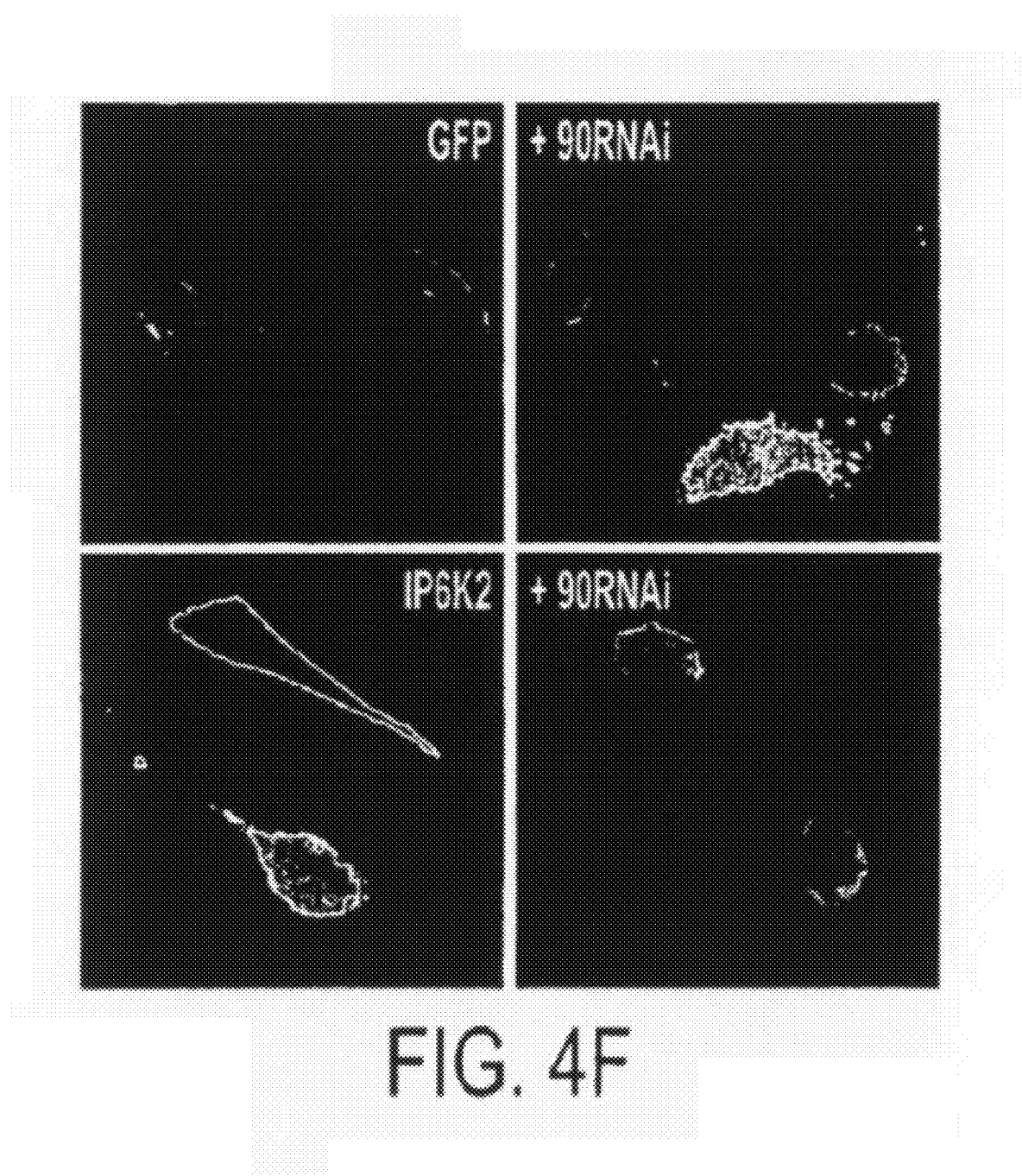
Figure 5A:
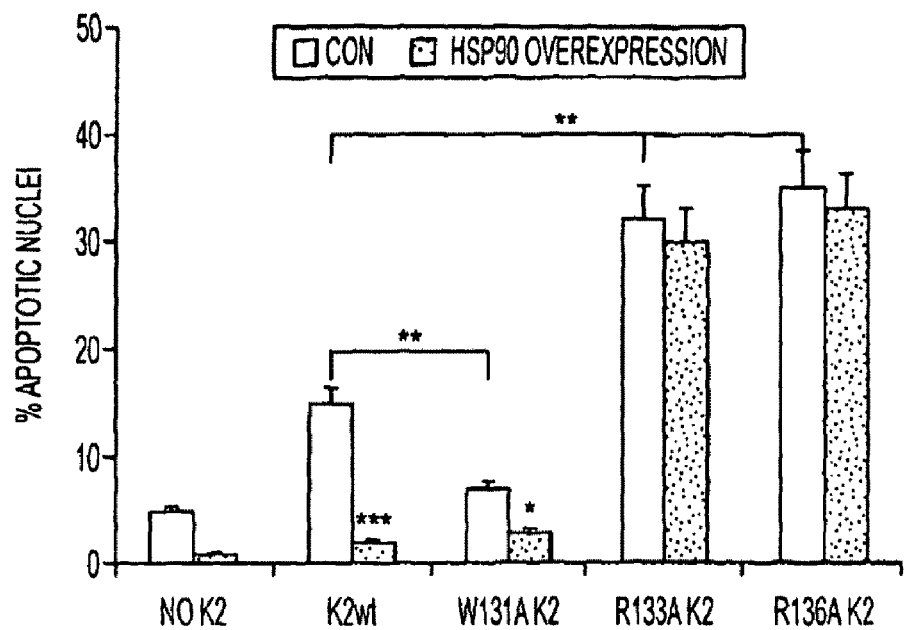
FIG. 5A-5F HSP90 negatively regulates IP6K2 mediated cell death.
Figure 5B:
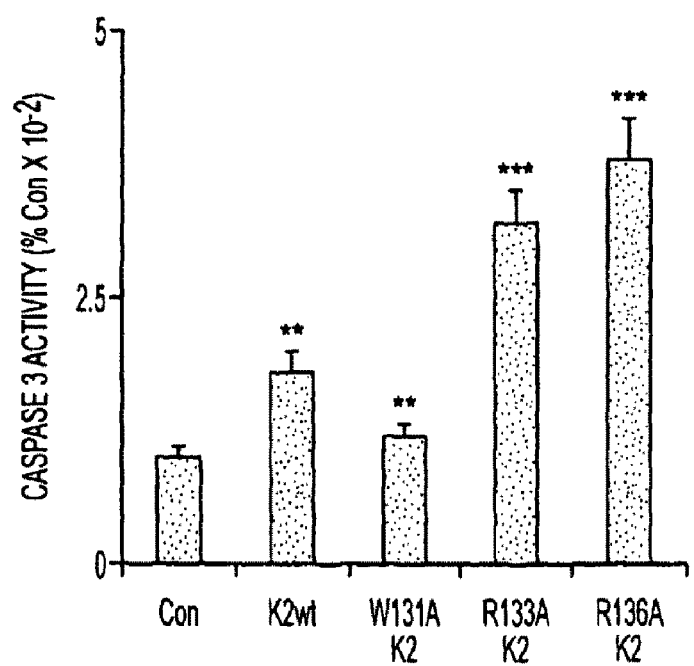
Figure 5C:
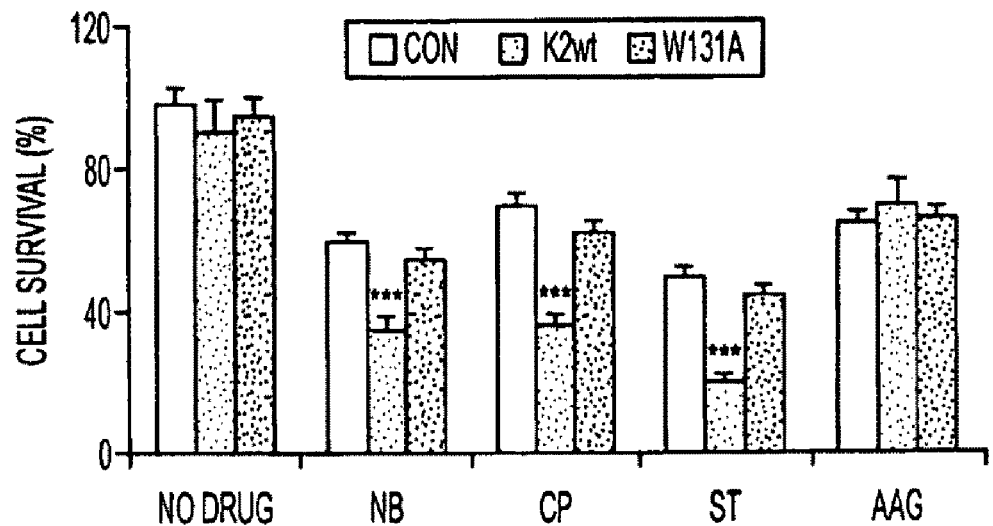
Figure 5D:
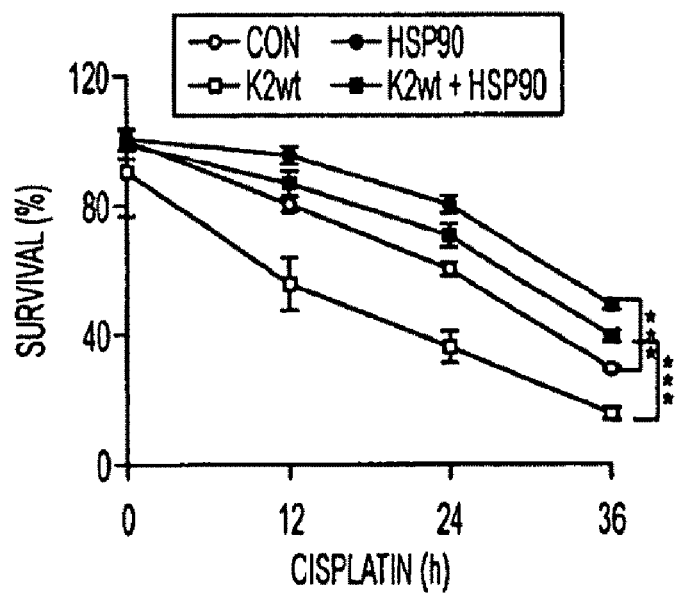
Figure 5E:
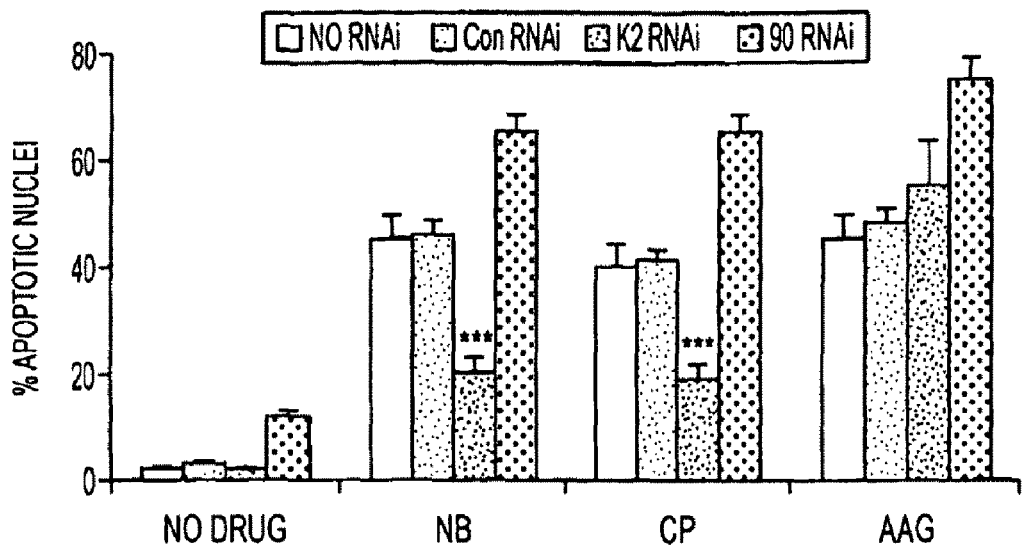
Figure 5F:
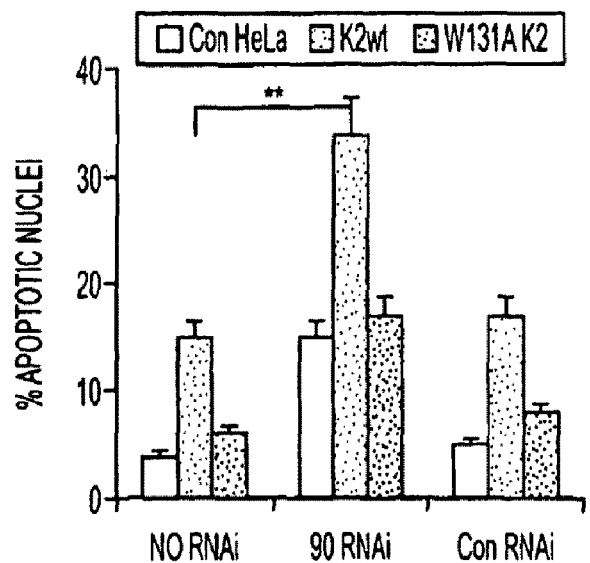

Depletion of HSP90 by RNA interference increases drug induced (FIG. 4E) and spontaneous (FIG. 4f) cell death of HeLa cells in control cells as well as cells transfected with IP6K2. The increased spontaneous cell death associated with HSP90 depletion is consistent with the well known cytoprotectant actions of HSP90. The marked augmentation of such cell death elicited by IP6K2 overexpression is consistent with the possibility that a significant portion of HSP90's physiologic cytoprotectant actions involves IP6K2.

Example 9

HSP90/IP6K2 Binding Affects Subcellular Localization

Figure 9A:
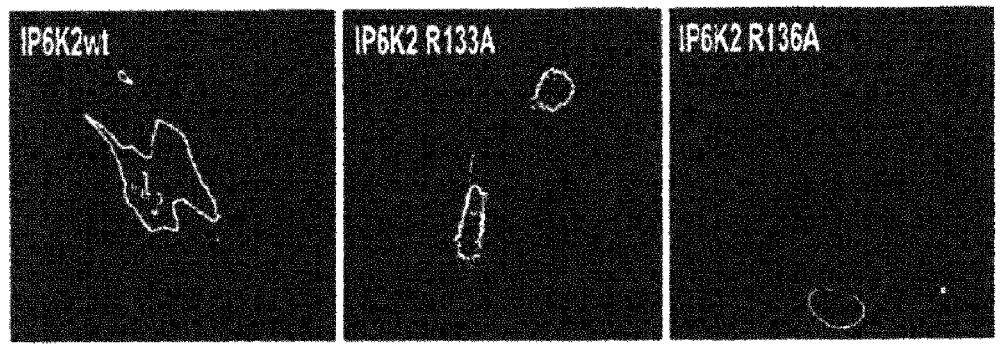
FIGS. 9A-9B.
Figure 9B:
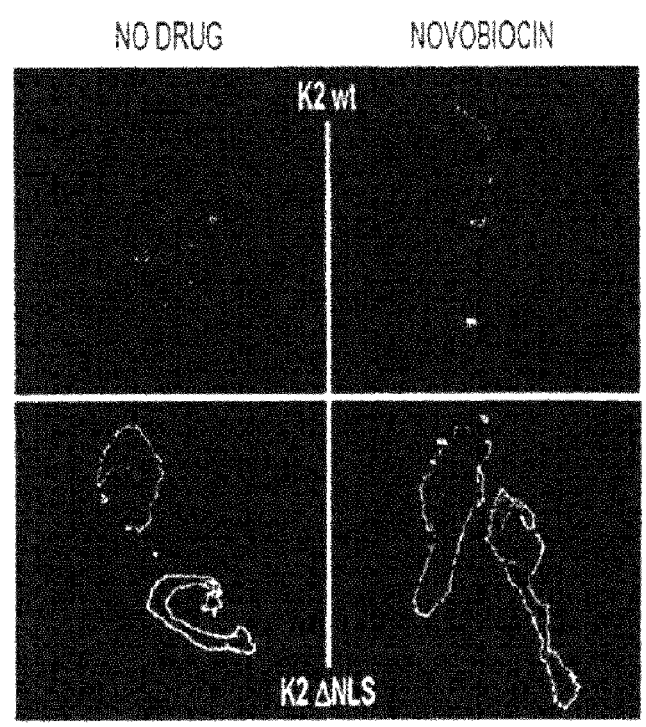

The intracellular localization of IP6K2 appears to vary with cell type and the mode of overexpression. During apoptosis we observed translocation of IP6K2 to a sub-population of mitochondria (10), while Morrison et al. (34) detected nuclear translocation of IP6K2 in interferon-associated apoptosis. In the present study novobiocin and cisplatin enhance nuclear levels of IP6K2 (FIGS. 8a, 8b, 8c and 9a, 9c, 9d), whereas AAG increases IP6K2 localization in the cytosol (FIG. 9b, 9c). HSP90 depletion leads to IP6K2 accumulation in the nucleus (FIG. 9g). IP6K2 mutants that do not bind to HSP90 also translocate to the nucleus (FIG. 9h). By contrast, in cells overexpressing HSP90, IP6K2 is predominantly cytosolic (FIG. 9f). As reported previously (10), staurosporine elicits mitochondrial translocation of IP6K2 (FIG. 9e). Thus, under basal conditions HSP90 retains IP6K2 in the cytosol in an inactive state, while disruption of the binding elicits translocation of the enzyme to different organelles.

Example 10

Methods

Methods

GDDA analysis: GDDA was performed as described previously (21, 22). Briefly we modified the original target sequence (hIP6K2a, gi|56237025|ref|NP_057375.2|) by inserting a portion (10-50%; "seed") of the p23 domain profile (cd00237; length 116 amino acids) at every amino acid position of the target sequence. This modification generated a library of 4,260 sequences with a "sliding" alignment initiation site. Each modified sequence was searched by rps-BLAST (settings E=0.01, no filter) against the "seed" domain sequence and the percentage of coverage (y-axis) were plotted against each amino acid position (x-axis).

Cloning and plasmid construction: HSP90α and HSP90β were cloned into pCMV-HA plasmids by RT-PCR using mRNA purified from HEK293 cells. pCMVHA+HSP90α plasmid was SalI-NotI digested and the full-length HSP90 gene was sucloned into pGEX4T-2. Deletion mutants (1-272, 273-732 and 629-732) of HSP90α were made by amplifying the regions with SalI-NotI site containing primers and were sub-cloned into pGEX4T-2 plasmid. For subcloning into pDsRed-C1 plasmid, full length HSP90α gene was amplified using primers containing BglII-BamHI sites.

Point mutants of IP6K2 were generated in either pCMV-Myc or pEGFP-C1 vector using the 'Quickchange Site-directed Mutagenesis protocol, (Stratagene). Mutation was confirmed by sequencing.

Cell culture: HeLa and HEK 293 were cultured as described (18). Cells were treated with cisplatin (30 μM), novobiocin (500 μM), staurosporine (1 μM) for 8 h or AAG (1 μM) overnight. HEK293 and HeLa cells were transiently transfected using polyfect transfection reagent (Qiagen). siRNAs were transfected with 'Hiperfect' transfection reagent (Qiagen).

IP7 measurement in vivo: HeLa cells were labeled with [$^3$H]inositol at 40% confluency in 6-well plates and were incubated for 3 days. Cells were transfected one day after inositol labeling. Following 48 h of transfection, cells were lysed and inositol phosphates were isolated by HPLC following standard procedure (3). IP6K activity in the cells was calculated as the ratio of [$^3$H]IP7 to [$^3$H]IP6. IP6K activity in the untransfected cells was designated 100%.

Yeast culture and IP7 measurement in HSP deficient yeast strains: Yeast wild-type and mutant for different HSP genes were purchased from Open Biosystems and IP7 was isolated by HPLC as previously described (38). IP6K activity in vivo was expressed as the IP7/IP6 ratio following labeling of cells with [$^3$H]inositol. Activity in the control cells was designated 100%.

Co-immunoprecipitation: Cells/mouse brain were homogenised in lysis buffer (20 mM Tris pH 7.4, 150 mM NaCl, 0.5% NP-40, and protease inhibitor cocktails). Equal amounts of protein were immunoprecipitated at 4° C. overnight using the protein A/G agarose beads in the presence of antibody. After immunoprecipitation, beads were washed four times with lysis buffer. Co-immunoprecipitates were resolved by SDS-PAGE and analysed by western blotting.

siRNA experiments: HeLa cells (50% confluent) were transfected with 50 nM IP6K2 (s-UAGAACUGAUGUUC-CCUUGGGACCA; SEQ ID NO: 5, a-UGGUCCCAAGG- GAACAUCAGUUCUA; SEQ ID NO: 6) or HSP90 (s-GCU-UAAAGUUGUAACAAAU; SEQ ID NO: 7, a-AUU UGU UAC AAC UUU AAG; SEQ ID NO: 8) siRNA for 48 h. For IP6K activity measurement in vivo, cells were labeled with [$^3$H]inositol one day before transfection and were incubated for 3 days.

Binding assay in vitro: One µg of each of the bacterially purified (GST) full-length or the deletion mutants of HSP90 was incubated with equal amounts of immunoprecipitated IP6K2 in 0.5 ml of the binding buffer containing 20 mM Tris-Cl, pH 7.4, 100 mM NaCl, 0.5% NP-40 and 0.25 mg/ml BSA at 4° C. for 2 h. The beads were washed (4×1 ml) with wash buffer (binding buffer containing 300 mM NaCl), separated by SDS-PAGE, and analysed by western blotting.

To determine inhibitory concentrations of various drugs in HSP90-IP6K2 interaction in vitro, 250 nM purified endogenous HSP90 (HeLa) was incubated with indicated concentrations of various drugs at 37° C. for 30 minutes in binding buffer (20 mM Tris 7.4, 1 mM DTT, 1 mM PMSF and protease inhibitor cocktail). The complex was added to purified myc-IP6K2 (immunoprecipitated from HEK 293 cells) and was incubated for 30 minutes at 37° C. The beads were washed three times with binding buffer and bound HSP90 was analyzed by blotting with anti-HSP90 monoclonal antibody.

IP6K activity in vitro: Equal concentrations of immunoprecipitated Myc-tagged proteins were used in the assay (confirmed by western blotting) in the presence of [$^3$H]IP6 and Mg-ATP as substrates using standard assay conditions (17) at 37° C. for 2 h. Synthesized IP7 was separated from IP6 by HPLC. Activities of mutant enzymes were calculated with WT-IP6K2 designated 100%.

Substrate binding assay: Equal concentrations of immunoprecipitated WT and mutant IP6K2 were incubated with 5 µM IP6 (containing 130 nCi [$^3$H]IP6) in a binding buffer containing 20 mM Tris-HCl, pH 7.4, 100 mM NaCl, 1 mM DTT for 30 min at 4° C. Beads were washed 3 times with the same buffer. Binding of [$^3$H]IP6 to the wild type enzyme was designated 100%. Untransfected beads were used as control.

Cell death assay: Cell death was determined using the MTT [3-(4,5-dimethylthiazol-2-yl)-2,5-diphenyl-2H-tetrazolium bromide] assay protocol. HeLa cells were transfected with 2 µg Myc-IP6K2 (WT or mutants) either alone or with 2 µg HA-HSP90. After 24 h, cells were added to a 96-well plate at a density of 5000 cells/well (200 µl volume) and allowed to adhere overnight. Cell death was induced by the following drug treatments: Cisplatin (30 µM), novobiocin (500 µM) and staurosporine (1 µM) for 8 h or AAG (1 µM) for overnight. Then, 50 µl of 2 mg/ml MTT solution were added to each well, and cells were incubated for 4 h at 37° C. Formazan crystals were dissolved in 100 µl of DMSO. Absorbance was measured at 570/630 nm on an ELISA reader. Cell death was calculated as $OD_{570}-OD_{630}$.

To assess cell death in siRNA treated HeLa cells, IP6K2 or HSP90 were depleted as described earlier. After 48 h of siRNA treatment, cells were transferred to a 96-well plate as 5000 cell/well. After one day, drugs were added and cell death monitored as described above.

Generation of stable HEK 293 cell lines expressing GFP-IP6K2: HEK293 cells were transfected with a plasmid (pEGFPC1) encoding IP6K2 under the control of the CMV promoter. This plasmid also encodes a neomycin resistance gene. Transfected cells were cultured in Dulbecco's modified Eagle's medium containing 10% fetal calf serum and 1 mg/ml Geneticin to select for stably transformed cells. After 6 weeks in culture, a cell line expressing GFP-IP6K2 was cloned from a single cell by limiting-dilution culturing.

Caspase 3 activity assay: Caspase 3 activity was tested using 'Caspase 3 colorimetric assay kit' from Biovision following manufacturer's protocol. After reaction, samples were read at 405-nm in a spectrophotometer using a 100-µl micro quartz. Caspase activity is presented as fold increase in OD405 as an average of three independent experiments.

Isolation of nuclei: Nuclei were separated from other cytoplasmic components using commercial kits (See 'Reagents' section). Preparation was checked each time by running appropriate controls for nucleus (p84).

Fluorescence microscopy: HeLa cells were transfected with pEGFP+IP6K1/IP6K2/IP6K3, either alone or with pDsRed HSP90α with or without drug or siRNA treatment, fixed with ice cold methanol, stained with Hoechst stain for nucleus and observed under an Ultraview1 confocal microscope.

MTT assay for cell Survival: Cell death was determined using the MTT [3-(4,5-dimethylthiazol-2-yl)-2,5-diphenyl-2H-tetrazolium bromide] assay protocol. HeLa cells were transfected with 2 µg myc-IP6K2 (WT or mutants) either alone or with 2 µg HA-HSP90. After 24 h, cells were added to a 96-well plate at a density of 5000 cells/well (200 µl volume) and allowed to adhere overnight. Cell death was induced by the following drug treatments: Cisplatin (30 µM O/N), novobiocin (500 µM, O/N) and staurosporine (1 µM) for 6 h or AAG (1 µM, O/N). Then, 50 µl of 2 mg/ml MTT solution were added to each well, and cells were incubated for 4 h at 37° C. Formazan crystals were dissolved in 100 µl of DMSO. Absorbance was measured at 570/630 nm on an ELISA reader. Cell death was calculated as OD570-OD630. To assess cell death in siRNA treated HeLa cells, IP6K2 or HSP90 were depleted as described earlier. After 48 h of siRNA treatment, cells were transferred to a 96-well plate as 5000 cell/well. After one day, drugs were added and cell death monitored as described above.

Quantification of Apoptosis: After the cells had been treated as described in each experiment, they were fixed rapidly with ice-cold methanol for 5 min. and then stained for 5 min. with Hoechst 33342 dye. After being washed with PBS, the cells were then observed under microscope. Apoptotic cells were identified by having condensed and/or fragmented chromatin in the nuclei. At least 250 cells from randomly selected fields were counted in each experiment.

Statistical analysis: All the experiments were repeated three times and ±S.D. was calculated. Significance of result was calculated by 'Paired Student's T-test' (*$P<0.05$, $P<0.01$, *$P<0.001$).

REFERENCE

The disclosure of each reference cited is expressly incorporated herein.
1. Berridge, M. J., Lipp, P., and Bootman, M. D. Signal transduction. The calcium entry pas de deux. *Science* 287, 1604-1605 (2000).
2. Irvine, R. F., and Schell, M. J. Back in the water: the return of the inositol phosphates. *Nat. Rev. Mol. Cell. Biol.* 2, 327-338 (2001).
3. Menniti, F., S. et al. Turnover of inositol pentakisphosphates, inositol polyphosphate pyrophosphates in pancreatoma cells. *J. Biol. Chem.* 268, 3850-6 (1993).
4. Stephens, L. et al. The detection, purification, structural characterization, and metabolism of diphosphoinositol pentakisphosphate(s) and bisdiphosphoinositol tetrakisphosphate(s). *J. Biol. Chem.* 268, 4009-15 (1993).

5. Luo, H., R. et al. Inositol pyrophosphates mediate chemotaxis in Dictyostelium via pleckstrin homology domain-PtdIns(3,4,5)P3 interactions. *Cell.* 114, 559-72 (2003).
6. Bennett, M. et al. Inositol pyrophosphates: metabolism and signaling. *Cell Mol. Life Sci.* 63, 552-64 (2006). Review.
7. Saiardi, A. et al. Phosphorylation of proteins by inositol pyrophosphates. *Science.* 306, 2101-5 (2004).
8. Saiardi, A. et al. Synthesis of diphosphoinositol pentakisphosphate by a newly identified family of higher inositol polyphosphate kinases. *Curr Biol.* 9, 1323-6 (1999).
9. Saiardi, A. et al. Identification and characterization of a novel inositol hexakisphosphate kinase. *J. Biol. Chem.* 276, 39179-85 (2001).
10. Nagata, E. et al. Inositol hexakisphosphate kinase-2, a physiologic mediator of cell death. *J. Biol. Chem.* 280, 1634-40 (2005).
11. Morrison, B., H. et al. Inositol hexakisphosphate kinase 2 sensitizes ovarian carcinoma cells to multiple cancer therapeutics. *Oncogene.* 21, 1882-9 (2002).
12. Morrison, B., H. et al. Inositol hexakisphosphate kinase 2 mediates growth suppressive and apoptotic effects of interferon-beta in ovarian carcinoma cells. *J. Biol. Chem.* 276, 24965-70 (2001).
13. Bruey, J. M. et al. Hsp27 negatively regulates cell death by interacting with cytochrome c. *Nature Cell Biol.* 2, 645-52 (2000).
14. Beere, H. M. et al. Heat-shock protein 70 inhibits apoptosis by preventing recruitment of procaspase-9 to the Apaf-1 apoptosome. *Nature Cell Biol.* 2, 469-75 (2000).
15. Dias, S. et al. VEGF (165) promotes survival of leukemic cells by Hsp90-mediated induction of Bcl-2 expression and apoptosis inhibition. *Blood.* 99, 2532-40 (2002).
16. Pandey, P. et al. Negative regulation of cytochrome c-mediated oligomerization of Apaf-1 and activation of procaspase-9 by heat shock protein 90. *EMBO J.* 19, 4310-22 (2000).
17. Eustace, B., K. et al. Functional proteomic screens reveal an essential extracellular role for HSP90 alpha in cancer cell invasiveness. *Nature Cell Biol.* 6, 507-14 (2004).
18. Bagatell, R. and Whitesell, L. Altered Hsp90 function in cancer: a unique therapeutic opportunity. *Mol Cancer Ther.* 3, 1021-30 (2004). Review.
19. Yu, X., M. et al. Hsp90 inhibitors identified from a library of novobiocin analogues. *J. Am. Chem. Soc.* 127, 12778-9 (2005).
20. Neckers, L. Hsp90 inhibitors as novel cancer chemotherapeutic agents. *Trends Mol. Med.* 8, S55-61 (2002) Review.
21. Kamal, A. et al. A high-affinity conformation of Hsp90 confers tumour selectivity on Hsp90 inhibitors. *Nature.* 425, 407-10 (2003).
22. Neckers, L. Development of small molecule Hsp90 inhibitors: utilizing both forward and reverse chemical genomics for drug identification. *Curr Med Chem.* 10, 733-9 (2003). Review.
23. van Rossum, D., B. et al. Phospholipase Cgamma1 controls surface expression of TRPC3 through an intermolecular PH domain. *Nature.* 434, 99-104 (2005).
24. Patterson, R., L. et al. Phospholipase C-gamma: diverse roles in receptor-mediated calcium signaling. *Trends Biochem Sci.* 30, 688-97 (2005). Review.
25. Weaver, A., J. et al. Crystal structure and activity of human p23, a heat shock protein 90 co-chaperone. *J. Biol. Chem.* 275, 23045-52 (2000).
26. Stebbins, C., E. et al. Crystal structure of an Hsp90-geldanamycin complex: targeting of a protein chaperone by an antitumor agent. *Cell.* 89, 239-50 (1997).
27. Cowen, L., E., and Lindquist, S., L. Hsp90 potentiates the rapid evolution of new traits: drug resistance in diverse fungi. *Science.* 309, 2185-9 (2005).
28. Marcu, M. G., Schulte, T., W., and Neckers, L. Novobiocin and related coumarins and depletion of heat shock protein 90-dependent signaling proteins. *J. Natl Cancer Inst.* 92, 242-8 (2000).
29. Rosenhagen, M., C. et al. The heat shock protein 90-targeting drug cisplatin selectively inhibits steroid receptor activation. *Mol. Endocrinol.* 17, 1991-2001 (2003).
30. Itoh, H. et al. A novel chaperone-activity-reducing mechanism of the 90-kDa molecular chaperone HSP90. *Biochem. J.* 343, 697-703 (1999).
31. Wang, X., Martindale, J. L., and Holbrook, N. J. Requirement for ERK activation in cisplatin-induced apoptosis. *J. Biol. Chem.* 275, 39435-43 (2000).
32. Malicet, C. et al. Regulation of apoptosis by the p8/prothymosin alpha complex. *Proc Natl Acad Sci USA.* 103, 2671-6 (2006).
33. Ali, M., M. et al. Crystal structure of an Hsp90-nucleotide-p23/Sba1 closed chaperone complex. *Nature.* 440, 1013-7 (2006).
34. Morrison, B., H. et al. Apo2L/TRAIL induction and nuclear translocation of inositol hexakisphosphate kinase 2 during IFN-beta-induced apoptosis in ovarian carcinoma. *Biochem. J.* 385, 595-603 (2005).
35. Soti, C., Racz, A., and Csermely, P. A Nucleotide-dependent molecular switch controls ATP binding at the C-terminal domain of Hsp90. N-terminal nucleotide binding unmasks a C-terminal binding pocket. *J. Biol. Chem.* 277, 7066-75 (2002).
36. Hill, M., M., and Hemmings, B., A. Inhibition of protein kinase B/Akt. Implications for cancer therapy. *Pharmacol. Ther.* 93, 243-51 (2002). Review.
37. Gescher, A. Staurosporine analogues—pharmacological toys or useful antitumour agents? *Crit. Rev. Oncol. Hematol.* 34, 127-35 (2000). Review.
38. Saiardi, A., Caffrey, J., J., Snyder, S., H. and Shears, S., B. Inositol polyphosphate multikinase (ArgRIII) determines nuclear mRNA export in *Saccharomyces cerevisiae*. *FEBS Lett.* 468, 28-32 (2000).

The invention claimed is:

1. A method of identifying compounds which interfere with the binding of human IP6K2 protein to human HSP90 protein, comprising:

contacting a cell with a test compound, wherein the cell comprises three recombinant DNA constructs,
said first construct encoding a first polypeptide fused to a sequence-specific DNA-binding domain,
said second construct encoding a second polypeptide fused to a transcriptional activation domain,
said third construct comprising a reporter gene downstream from a DNA element which is recognized by said sequence-specific DNA-binding domain,
wherein said first polypeptide is a IP6K2 polypeptide and said second polypeptide is a HSP90 polypeptide, or said first polypeptide is a HSP90 polypeptide and said second polypeptide is a IP6K2 polypeptide; wherein said HSP90 polypeptide comprises amino acids 751-854 of SEQ ID NO: 2 or amino acids 630-731 of SEQ ID NO: 3 and said IP6K2 polypeptide comprises amino acids 131-140 of SEQ ID NO: 1;
determining quantity of expression of the reporter gene in the presence of said compound, wherein a decrease in the expression of the reporter gene in the presence of the compound indicates that the compound interferes with the binding of human IP6K2 protein to human HSP90.

2. An isolated cell which comprises three recombinant DNA constructs,
said first construct encoding a first polypeptide fused to a sequence-specific DNA-binding domain,
said second construct encoding a second polypeptide fused to a transcriptional activation domain,
said third construct comprising a reporter gene downstream from a DNA element which is recognized by said sequence-specific DNA-binding domain,
wherein said first polypeptide is an IP6K2 polypeptide and said second polypeptide is a HSP90 polypeptide, or said first polypeptide is a HSP90 polypeptide and said second polypeptide is an IP6K2 polypeptide; wherein said HSP90 polypeptide comprises amino acids 751-854 of SEQ ID NO: 2 or amino acids 630-731 of SEQ ID NO: 3 and said IP6K2 polypeptide comprises amino acids 131-140 of SEQ ID NO: 1.

* * * * *

SEQUENCE LISTING

<160> NUMBER OF SEQ ID NOS: 8

<210> SEQ ID NO 1
<211> LENGTH: 426
<212> TYPE: PRT
<213> ORGANISM: Homo sapiens

<400> SEQUENCE: 1

```
Met Ser Pro Ala Phe Arg Ala Met Asp Val Glu Pro Arg Ala Lys Gly
  1               5                  10                  15
Val Leu Leu Glu Pro Phe Val His Gln Val Gly His Ser Cys Val
             20                  25                  30
Leu Arg Phe Asn Glu Thr Thr Leu Cys Lys Pro Leu Val Pro Arg Glu
             35                  40                  45
His Gln Phe Tyr Glu Thr Leu Pro Ala Glu Met Arg Lys Phe Thr Pro
     50                  55                  60
Gln Tyr Lys Gly Val Val Ser Val Arg Phe Glu Asp Glu Asp Arg
 65                  70                  75                  80
Asn Leu Cys Leu Ile Ala Tyr Pro Leu Lys Gly Asp His Gly Ile Val
                 85                  90                  95
Asp Ile Val Asp Asn Ser Asp Cys Glu Pro Lys Ser Lys Leu Leu Arg
                100                 105                 110
Trp Thr Thr Asn Lys Lys His His Val Leu Glu Thr Glu Lys Thr Pro
             115                 120                 125
Lys Asp Trp Val Arg Gln His Arg Lys Glu Glu Lys Met Lys Ser His
    130                 135                 140
Lys Leu Glu Glu Glu Phe Glu Trp Leu Lys Lys Ser Glu Val Leu Tyr
145                 150                 155                 160
Tyr Thr Val Glu Lys Lys Gly Asn Ile Ser Ser Gln Leu Lys His Tyr
                165                 170                 175
Asn Pro Trp Ser Met Lys Cys His Gln Gln Leu Gln Arg Met Lys
             180                 185                 190
Glu Asn Ala Lys His Arg Asn Gln Tyr Lys Phe Ile Leu Leu Glu Asn
            195                 200                 205
Leu Thr Ser Arg Tyr Glu Val Pro Cys Val Leu Asp Leu Lys Met Gly
    210                 215                 220
Thr Arg Gln His Gly Asp Asp Ala Ser Glu Glu Lys Ala Ala Asn Gln
225                 230                 235                 240
Ile Arg Lys Cys Gln Gln Ser Thr Ser Ala Val Ile Gly Val Arg Val
                245                 250                 255
Cys Gly Met Gln Val Tyr Gln Ala Gly Ser Gly Gln Leu Met Phe Met
            260                 265                 270
Asn Lys Tyr His Gly Arg Lys Leu Ser Val Gln Gly Phe Lys Glu Ala
        275                 280                 285
Leu Phe Gln Phe Phe His Asn Gly Arg Tyr Leu Arg Arg Glu Leu Leu
    290                 295                 300
Gly Pro Val Leu Lys Lys Leu Thr Glu Leu Lys Ala Val Leu Glu Arg
305                 310                 315                 320
Gln Glu Ser Tyr Arg Phe Tyr Ser Ser Ser Leu Leu Val Ile Tyr Asp
                325                 330                 335
Gly Lys Glu Arg Pro Glu Val Val Leu Asp Ser Asp Ala Glu Asp Leu
            340                 345                 350
Glu Asp Leu Ser Glu Glu Ser Ala Asp Glu Ser Ala Gly Ala Tyr Ala
        355                 360                 365
Tyr Lys Pro Ile Gly Ala Ser Ser Val Asp Val Arg Met Ile Asp Phe
    370                 375                 380
Ala His Thr Thr Cys Arg Leu Tyr Gly Glu Asp Thr Val Val His Glu
385                 390                 395                 400
Gly Gln Asp Ala Gly Tyr Ile Phe Gly Leu Gln Ser Leu Ile Asp Ile
                405                 410                 415
Val Thr Glu Ile Ser Glu Glu Ser Gly Glu
            420                 425
```

<210> SEQ ID NO 2
<211> LENGTH: 854
<212> TYPE: PRT
<213> ORGANISM: Homo sapiens

<400> SEQUENCE: 2

Met Pro Pro Cys Ser Gly Gly Asp Gly Ser Thr Pro Gly Pro Ser
1               5                   10                  15

Leu Arg Asp Arg Asp Cys Pro Ala Gln Ser Ala Glu Tyr Pro Arg Asp
                20                  25                  30

Arg Leu Asp Pro Arg Pro Gly Ser Pro Ser Glu Ala Ser Ser Pro Pro
                35                  40                  45

Phe Leu Arg Ser Arg Ala Pro Val Asn Trp Tyr Gln Glu Lys Ala Gln
    50                  55                  60

Val Phe Leu Trp His Leu Leu Val Ser Gly Ser Thr Thr Leu Leu Cys
65                  70                  75                  80

Leu Trp Lys Gln Pro Phe His Val Ser Ala Phe Pro Val Thr Ala Ser
                85                  90                  95

Leu Ala Phe Arg Gln Ser Gln Gly Ala Gly Gln His Leu Tyr Lys Asp
                100                 105                 110

Leu Gln Pro Phe Ile Leu Arg Leu Leu Met Pro Glu Glu Thr Gln
                115                 120                 125

Thr Gln Asp Gln Pro Met Glu Glu Glu Val Glu Thr Phe Ala Phe
            130                 135                 140

Gln Ala Glu Ile Ala Gln Leu Met Ser Leu Ile Ile Asn Thr Phe Tyr
145                 150                 155                 160

Ser Asn Lys Glu Ile Phe Leu Arg Glu Leu Ile Ser Asn Ser Ser Asp
                165                 170                 175

Ala Leu Asp Lys Ile Arg Tyr Glu Ser Leu Thr Asp Pro Ser Lys Leu
                180                 185                 190

Asp Ser Gly Arg Glu Leu His Ile Asn Leu Ile Pro Asn Lys Gln Gly
                195                 200                 205

Arg Thr Leu Thr Ile Val Asp Thr Gly Ile Gly Met Thr Lys Ala Asp
            210                 215                 220

Leu Ile Asn Asn Leu Gly Thr Ile Ala Lys Ser Gly Thr Lys Ala Phe
225                 230                 235                 240

Met Glu Ala Leu Gln Ala Gly Ala Asp Ile Ser Met Ile Gly Gln Phe
                245                 250                 255

Gly Val Gly Phe Tyr Ser Ala Tyr Leu Val Ala Glu Lys Val Thr Val
                260                 265                 270

Ile Thr Lys His Asn Asp Asp Glu Gln Tyr Ala Trp Glu Ser Ser Ala
                275                 280                 285

Gly Gly Ser Phe Thr Val Arg Thr Asp Thr Gly Glu Pro Met Gly Arg
            290                 295                 300

Gly Thr Lys Val Ile Leu His Leu Lys Glu Asp Gln Thr Glu Tyr Leu
305                 310                 315                 320

Glu Glu Arg Arg Ile Lys Glu Ile Val Lys Lys His Ser Gln Phe Ile
                325                 330                 335

Gly Tyr Pro Ile Thr Leu Phe Val Glu Lys Glu Arg Asp Lys Glu Val
                340                 345                 350

Ser Asp Asp Glu Ala Glu Glu Lys Glu Asp Lys Glu Glu Glu Lys Glu
            355                 360                 365

Lys Glu Glu Lys Glu Ser Glu Asp Lys Pro Glu Ile Glu Asp Val Gly
            370                 375                 380

```
Ser Asp Glu Glu Glu Lys Lys Asp Gly Asp Lys Lys Lys Lys
385                 390                 395                 400

Lys Ile Lys Glu Lys Tyr Ile Asp Gln Glu Leu Asn Lys Thr Lys
            405                 410                 415

Pro Ile Trp Thr Arg Asn Pro Asp Ile Thr Asn Glu Glu Tyr Gly
            420                 425                 430

Glu Phe Tyr Lys Ser Leu Thr Asn Asp Trp Glu Asp His Leu Ala Val
            435                 440                 445

Lys His Phe Ser Val Glu Gly Gln Leu Glu Arg Ala Leu Leu Phe
        450                 455                 460

Val Pro Arg Arg Ala Pro Phe Asp Leu Phe Glu Asn Arg Lys Lys
465                 470                 475                 480

Asn Asn Ile Lys Leu Tyr Val Arg Arg Val Phe Ile Met Asp Asn Cys
                485                 490                 495

Glu Glu Leu Ile Pro Glu Tyr Leu Asn Phe Ile Arg Gly Val Val Asp
                500                 505                 510

Ser Glu Asp Leu Pro Leu Asn Ile Ser Arg Glu Met Leu Gln Gln Ser
        515                 520                 525

Lys Ile Leu Lys Val Ile Arg Lys Asn Leu Val Lys Lys Cys Leu Glu
        530                 535                 540

Leu Phe Thr Glu Leu Ala Glu Asp Lys Glu Asn Tyr Lys Lys Phe Tyr
545                 550                 555                 560

Glu Gln Phe Ser Lys Asn Ile Lys Leu Gly Ile His Glu Asp Ser Gln
                565                 570                 575

Asn Arg Lys Lys Leu Ser Glu Leu Leu Arg Tyr Tyr Thr Ser Ala Ser
            580                 585                 590

Gly Asp Glu Met Val Ser Leu Lys Asp Tyr Cys Thr Arg Met Lys Glu
            595                 600                 605

Asn Gln Lys His Ile Tyr Tyr Ile Thr Gly Glu Thr Lys Asp Gln Val
        610                 615                 620

Ala Asn Ser Ala Phe Val Glu Arg Leu Arg Lys His Gly Leu Glu Val
625                 630                 635                 640

Ile Tyr Met Ile Glu Pro Ile Asp Glu Tyr Cys Val Gln Gln Leu Lys
                645                 650                 655

Glu Phe Glu Gly Lys Thr Leu Val Ser Val Thr Lys Glu Gly Leu Glu
                660                 665                 670

Leu Pro Glu Asp Glu Glu Glu Lys Lys Lys Gln Glu Glu Lys Lys Thr
        675                 680                 685

Lys Phe Glu Asn Leu Cys Lys Ile Met Lys Asp Ile Leu Glu Lys Lys
        690                 695                 700

Val Glu Lys Val Val Val Ser Asn Arg Leu Val Thr Ser Pro Cys Cys
705                 710                 715                 720

Ile Val Thr Ser Thr Tyr Gly Trp Thr Ala Asn Met Glu Arg Ile Met
                725                 730                 735

Lys Ala Gln Ala Leu Arg Asp Asn Ser Thr Met Gly Tyr Met Ala Ala
            740                 745                 750

Lys Lys His Leu Glu Ile Asn Pro Asp His Ser Ile Ile Glu Thr Leu
        755                 760                 765

Arg Gln Lys Ala Glu Ala Asp Lys Asn Asp Lys Ser Val Lys Asp Leu
        770                 775                 780

Val Ile Leu Leu Tyr Glu Thr Ala Leu Leu Ser Ser Gly Phe Ser Leu
785                 790                 795                 800

Glu Asp Pro Gln Thr His Ala Asn Arg Ile Tyr Arg Met Ile Lys Leu
```

```
                        805                 810                 815
Gly Leu Gly Ile Asp Glu Asp Pro Thr Ala Asp Thr Ser Ala
            820                 825                 830

Ala Val Thr Glu Glu Met Pro Pro Leu Glu Gly Asp Asp Thr Ser
            835                 840                 845

Arg Met Glu Glu Val Asp
    850

<210> SEQ ID NO 3
<211> LENGTH: 732
<212> TYPE: PRT
<213> ORGANISM: Homo sapiens

<400> SEQUENCE: 3

Met Pro Glu Glu Thr Gln Thr Gln Asp Gln Pro Met Glu Glu Glu
  1               5                  10                  15

Val Glu Thr Phe Ala Phe Gln Ala Glu Ile Ala Gln Leu Met Ser Leu
                 20                  25                  30

Ile Ile Asn Thr Phe Tyr Ser Asn Lys Glu Ile Phe Leu Arg Glu Leu
                 35                  40                  45

Ile Ser Asn Ser Ser Asp Ala Leu Asp Lys Ile Arg Tyr Glu Thr Leu
 50                  55                  60

Thr Asp Pro Ser Lys Leu Asp Ser Gly Lys Glu Leu His Ile Asn Leu
 65                  70                  75                  80

Ile Pro Asn Lys Gln Asp Arg Thr Leu Thr Ile Val Asp Thr Gly Ile
                 85                  90                  95

Gly Met Thr Lys Ala Asp Leu Ile Asn Asn Leu Gly Thr Ile Ala Lys
                100                 105                 110

Ser Gly Thr Lys Ala Phe Met Glu Ala Leu Gln Ala Gly Ala Asp Ile
                115                 120                 125

Ser Met Ile Gly Gln Phe Gly Val Gly Phe Tyr Ser Ala Tyr Leu Val
                130                 135                 140

Ala Glu Lys Val Thr Val Ile Thr Lys His Asn Asp Asp Glu Gln Tyr
145                 150                 155                 160

Ala Trp Glu Ser Ser Ala Gly Gly Ser Phe Thr Val Arg Thr Asp Thr
                165                 170                 175

Gly Glu Pro Met Gly Arg Gly Thr Lys Val Ile Leu His Leu Lys Glu
                180                 185                 190

Asp Gln Thr Glu Tyr Leu Glu Glu Arg Arg Ile Lys Glu Ile Val Lys
                195                 200                 205

Lys His Ser Gln Phe Ile Gly Tyr Pro Ile Thr Leu Phe Val Glu Lys
210                 215                 220

Glu Arg Asp Lys Glu Val Ser Asp Asp Glu Ala Glu Glu Lys Glu Asp
225                 230                 235                 240

Lys Glu Glu Glu Lys Glu Lys Glu Glu Lys Glu Ser Glu Asp Lys Pro
                245                 250                 255

Glu Ile Glu Asp Val Gly Ser Asp Glu Glu Glu Glu Lys Lys Asp Gly
                260                 265                 270

Asp Lys Lys Lys Lys Lys Ile Lys Glu Lys Tyr Ile Asp Gln Glu
            275                 280                 285

Glu Leu Asn Lys Thr Lys Pro Ile Trp Thr Arg Asn Pro Asp Asp Ile
                290                 295                 300

Thr Asn Glu Glu Tyr Gly Glu Phe Tyr Lys Ser Leu Thr Asn Asp Trp
305                 310                 315                 320

Glu Asp His Leu Ala Val Lys His Phe Ser Val Glu Gly Gln Leu Glu
```

```
                        325                 330                 335
    Phe Arg Ala Leu Leu Phe Val Pro Arg Ala Pro Phe Asp Leu Phe
                    340                 345                 350
    Glu Asn Arg Lys Lys Asn Asn Ile Lys Leu Tyr Val Arg Arg Val
                355                 360                 365
    Phe Ile Met Asp Asn Cys Glu Glu Leu Ile Pro Glu Tyr Leu Asn Phe
    370                 375                 380
    Ile Arg Gly Val Val Asp Ser Glu Asp Leu Pro Leu Asn Ile Ser Arg
    385                 390                 395                 400
    Glu Met Leu Gln Gln Ser Lys Ile Leu Lys Val Ile Arg Lys Asn Leu
                    405                 410                 415
    Val Lys Lys Cys Leu Glu Leu Phe Thr Glu Leu Ala Glu Asp Lys Glu
                420                 425                 430
    Asn Tyr Lys Lys Phe Tyr Glu Gln Phe Ser Lys Asn Ile Lys Leu Gly
                435                 440                 445
    Ile His Glu Asp Ser Gln Asn Arg Lys Lys Leu Ser Glu Leu Leu Arg
    450                 455                 460
    Tyr Tyr Thr Ser Ala Ser Gly Asp Glu Met Val Ser Leu Lys Asp Tyr
    465                 470                 475                 480
    Cys Thr Arg Met Lys Glu Asn Gln Lys His Ile Tyr Tyr Ile Thr Gly
                    485                 490                 495
    Glu Thr Lys Asp Gln Val Ala Asn Ser Ala Phe Val Glu Arg Leu Arg
                500                 505                 510
    Lys His Gly Leu Glu Val Ile Tyr Met Ile Glu Pro Ile Asp Glu Tyr
                515                 520                 525
    Cys Val Gln Gln Leu Lys Glu Phe Glu Gly Lys Thr Leu Val Ser Val
    530                 535                 540
    Thr Lys Glu Gly Leu Glu Leu Pro Glu Asp Glu Glu Lys Lys Lys
    545                 550                 555                 560
    Gln Glu Glu Lys Lys Thr Lys Phe Glu Asn Leu Cys Lys Ile Met Lys
                    565                 570                 575
    Asp Ile Leu Glu Lys Lys Val Glu Lys Val Val Val Ser Asn Arg Leu
                580                 585                 590
    Val Thr Ser Pro Cys Cys Ile Val Thr Ser Thr Tyr Gly Trp Thr Ala
                595                 600                 605
    Asn Met Glu Arg Ile Met Lys Ala Gln Ala Leu Arg Asp Asn Ser Thr
                610                 615                 620
    Met Gly Tyr Met Ala Ala Lys Lys His Leu Glu Ile Asn Pro Asp His
    625                 630                 635                 640
    Ser Ile Ile Glu Thr Leu Arg Gln Lys Ala Glu Ala Asp Lys Asn Asp
                    645                 650                 655
    Lys Ser Val Lys Asp Leu Val Ile Leu Leu Tyr Glu Thr Ala Leu Leu
                660                 665                 670
    Ser Ser Gly Phe Ser Leu Glu Asp Pro Gln Thr His Ala Asn Arg Ile
                675                 680                 685
    Tyr Arg Met Ile Lys Leu Gly Leu Gly Ile Asp Glu Asp Asp Pro Thr
                690                 695                 700
    Ala Asp Asp Thr Ser Ala Ala Val Thr Glu Glu Met Pro Pro Leu Glu
    705                 710                 715                 720
    Gly Asp Asp Asp Thr Ser Arg Met Glu Glu Val Asp
                    725                 730

<210> SEQ ID NO 4
<211> LENGTH: 724
```

<212> TYPE: PRT
<213> ORGANISM: Homo sapiens

<400> SEQUENCE: 4

Met Pro Glu Glu Val His His Gly Glu Glu Val Glu Thr Phe Ala
1               5                   10                  15

Phe Gln Ala Glu Ile Ala Gln Leu Met Ser Leu Ile Ile Asn Thr Phe
            20                  25                  30

Tyr Ser Asn Lys Glu Ile Phe Leu Arg Glu Leu Ile Ser Asn Ala Ser
        35                  40                  45

Asp Ala Leu Asp Lys Ile Arg Tyr Glu Ser Leu Thr Asp Pro Ser Lys
    50                  55                  60

Leu Asp Ser Gly Lys Glu Leu Lys Ile Asp Ile Ile Pro Asn Pro Gln
65                  70                  75                  80

Glu Arg Thr Leu Thr Leu Val Asp Thr Gly Ile Gly Met Thr Lys Ala
                85                  90                  95

Asp Leu Ile Asn Asn Leu Gly Thr Ile Ala Lys Ser Gly Thr Lys Ala
            100                 105                 110

Phe Met Glu Ala Leu Gln Ala Gly Ala Asp Ile Ser Met Ile Gly Gln
        115                 120                 125

Phe Gly Val Gly Phe Tyr Ser Ala Tyr Leu Val Ala Glu Lys Val Val
    130                 135                 140

Val Ile Thr Lys His Asn Asp Asp Glu Gln Tyr Ala Trp Glu Ser Ser
145                 150                 155                 160

Ala Gly Gly Ser Phe Thr Val Arg Ala Asp His Gly Glu Pro Ile Gly
                165                 170                 175

Arg Gly Thr Lys Val Ile Leu His Leu Lys Glu Asp Gln Thr Glu Tyr
            180                 185                 190

Leu Glu Glu Arg Arg Val Lys Glu Val Val Lys Lys His Ser Gln Phe
        195                 200                 205

Ile Gly Tyr Pro Ile Thr Leu Tyr Leu Glu Lys Glu Arg Glu Lys Glu
    210                 215                 220

Ile Ser Asp Asp Glu Ala Glu Glu Lys Gly Glu Lys Glu Glu Glu
225                 230                 235                 240

Asp Lys Asp Asp Glu Glu Lys Pro Lys Ile Glu Asp Val Gly Ser Asp
                245                 250                 255

Glu Glu Asp Asp Ser Gly Lys Asp Lys Lys Lys Thr Lys Lys Ile
            260                 265                 270

Lys Glu Lys Tyr Ile Asp Gln Glu Glu Leu Asn Lys Thr Lys Pro Ile
        275                 280                 285

Trp Thr Arg Asn Pro Asp Asp Ile Thr Gln Glu Glu Tyr Gly Glu Phe
    290                 295                 300

Tyr Lys Ser Leu Thr Asn Asp Trp Glu Asp His Leu Ala Val Lys His
305                 310                 315                 320

Phe Ser Val Glu Gly Gln Leu Glu Phe Arg Ala Leu Leu Phe Ile Pro
                325                 330                 335

Arg Arg Ala Pro Phe Asp Leu Phe Glu Asn Lys Lys Lys Lys Asn Asn
            340                 345                 350

Ile Lys Leu Tyr Val Arg Arg Val Phe Ile Met Asp Ser Cys Asp Glu
        355                 360                 365

Leu Ile Pro Glu Tyr Leu Asn Phe Ile Arg Gly Val Val Asp Ser Glu
    370                 375                 380

Asp Leu Pro Leu Asn Ile Ser Arg Glu Met Leu Gln Gln Ser Lys Ile
385                 390                 395                 400

```
Leu Lys Val Ile Arg Lys Asn Ile Val Lys Lys Cys Leu Glu Leu Phe
            405                 410                 415
Ser Glu Leu Ala Glu Asp Lys Glu Asn Tyr Lys Lys Phe Tyr Glu Ala
        420                 425                 430
Phe Ser Lys Asn Leu Lys Leu Gly Ile His Glu Asp Ser Thr Asn Arg
            435                 440                 445
Arg Arg Leu Ser Glu Leu Leu Arg Tyr His Thr Ser Gln Ser Gly Asp
    450                 455                 460
Glu Met Thr Ser Leu Ser Glu Tyr Val Ser Arg Met Lys Glu Thr Gln
465                 470                 475                 480
Lys Ser Ile Tyr Tyr Ile Thr Gly Glu Ser Lys Glu Gln Val Ala Asn
                485                 490                 495
Ser Ala Phe Val Glu Arg Val Arg Lys Arg Gly Phe Glu Val Val Tyr
            500                 505                 510
Met Thr Glu Pro Ile Asp Glu Tyr Cys Val Gln Gln Leu Lys Glu Phe
        515                 520                 525
Asp Gly Lys Ser Leu Val Ser Val Thr Lys Glu Gly Leu Glu Leu Pro
    530                 535                 540
Glu Asp Glu Glu Glu Lys Lys Met Glu Glu Ser Lys Ala Lys Phe
545                 550                 555                 560
Glu Asn Leu Cys Lys Leu Met Lys Glu Ile Leu Asp Lys Lys Val Glu
                565                 570                 575
Lys Val Thr Ile Ser Asn Arg Leu Val Ser Ser Pro Cys Cys Ile Val
            580                 585                 590
Thr Ser Thr Tyr Gly Trp Thr Ala Asn Met Glu Arg Ile Met Lys Ala
        595                 600                 605
Gln Ala Leu Arg Asp Asn Ser Thr Met Gly Tyr Met Met Ala Lys Lys
    610                 615                 620
His Leu Glu Ile Asn Pro Asp His Pro Ile Val Glu Thr Leu Arg Gln
625                 630                 635                 640
Lys Ala Glu Ala Asp Lys Asn Asp Lys Ala Val Lys Asp Leu Val Val
                645                 650                 655
Leu Leu Phe Glu Thr Ala Leu Leu Ser Ser Gly Phe Ser Leu Glu Asp
            660                 665                 670
Pro Gln Thr His Ser Asn Arg Ile Tyr Arg Met Ile Lys Leu Gly Leu
        675                 680                 685
Gly Ile Asp Glu Asp Glu Val Ala Ala Glu Glu Pro Asn Ala Ala Val
    690                 695                 700
Pro Asp Glu Ile Pro Pro Leu Glu Gly Asp Glu Asp Ala Ser Arg Met
705                 710                 715                 720
Glu Glu Val Asp

<210> SEQ ID NO 5
<211> LENGTH: 25
<212> TYPE: RNA
<213> ORGANISM: Homo sapiens

<400> SEQUENCE: 5
uagaacugau gucccuugg gacca                                          25

<210> SEQ ID NO 6
<211> LENGTH: 25
<212> TYPE: RNA
<213> ORGANISM: Homo sapiens

<400> SEQUENCE: 6
```

```
uggucccaag ggaacaucag uucua                                        25

<210> SEQ ID NO 7
<211> LENGTH: 19
<212> TYPE: RNA
<213> ORGANISM: Homo sapiens

<400> SEQUENCE: 7
gcuuaaaguu guaacaaau                                               19

<210> SEQ ID NO 8
<211> LENGTH: 18
<212> TYPE: RNA
<213> ORGANISM: Homo sapiens

<400> SEQUENCE: 8
auuuguuaca acuuuaag                                                18
```